US012667833B2

(12) United States Patent
Elsharif et al.

(10) Patent No.: US 12,667,833 B2
(45) Date of Patent: Jun. 30, 2026

(54) NANOHYBRID CATALYST FOR HYDROGENATION REACTIONS

(71) Applicant: Imam Abdulrahman Bin Faisal University, Dammam (SA)

(72) Inventors: Asma Mohammed Zamil Elsharif, Dammam (SA); Monerah Ahmed Hassan Almarzooq, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 468 days.

(21) Appl. No.: 18/470,913

(22) Filed: Sep. 20, 2023

(65) Prior Publication Data

US 2025/0091041 A1 Mar. 20, 2025

(51) Int. Cl.
| | |
|---|---|
| C07C 33/22 | (2006.01) |
| B01J 23/52 | (2006.01) |
| B01J 31/02 | (2006.01) |
| B01J 31/26 | (2006.01) |
| B01J 35/23 | (2024.01) |
| B01J 35/30 | (2024.01) |
| B01J 35/45 | (2024.01) |
| B01J 35/50 | (2024.01) |
| B01J 35/64 | (2024.01) |
| B01J 37/02 | (2006.01) |
| B01J 37/04 | (2006.01) |
| C07C 29/141 | (2006.01) |

(52) U.S. Cl.
CPC ............... B01J 31/26 (2013.01); B01J 23/52 (2013.01); B01J 31/0209 (2013.01); B01J 35/23 (2024.01); B01J 35/393 (2024.01); B01J 35/45 (2024.01); B01J 35/50 (2024.01); B01J 35/653 (2024.01); B01J 35/657 (2024.01); B01J 37/0219 (2013.01); B01J 37/0221 (2013.01); B01J 37/0225 (2013.01); B01J 37/0236 (2013.01); B01J 37/04 (2013.01); C07C 33/22 (2013.01); B01J 2231/646 (2013.01); B01J 2531/18 (2013.01)

(58) Field of Classification Search
CPC ........ C07C 33/22; C07C 29/141; B01J 31/26; B01J 35/45; B01J 23/52
See application file for complete search history.

(56) References Cited

U.S. PATENT DOCUMENTS 8,889,429 B2 11/2014 Cao et al.

OTHER PUBLICATIONS

Razak et al. ; Catalytic reduction of 4-nitrophenol over biostabilized gold nanoparticles supported onto thioctic acid functionalized silica-coated magnetite nanoparticles and optimization using response surface methodology ; Inorganic and Nano-Metal Chemistry ; Feb. 4, 2020 ; 14 Pages.
Nasehi et al. ; Glucose Sensing Based on the Interaction of Gold Nanoparticles@Linoleic Acid With the Glucose ; IEEE Sensors Journal, vol. 22, Issue 7 ; Abstract Only ; 2 Pages.

*Primary Examiner* — Sikarl A Witherspoon

(74) *Attorney, Agent, or Firm* — Oblon, McClelland, Maier & Neustadt, L.L.P.

(57) ABSTRACT

A nanohybrid material includes a plurality of gold nanohybrid particles having formula (I). The gold nanohybrid particles have a gold nanoparticle (AuNPs) core and a shell of at least one fatty acid derivative at least partially disposed around the AuNPs core. The AuNPs core has a cuboidal shape and an average particle size of 20 to 60 nanometers (nm). Each $R_1$, and $R_2$ are independently selected from the group consisting of a hydrogen atom, and a fatty acid hydrocarbon chain having 16 to 22 carbon atoms. $R_3$ is selected from the group consisting of a hydrogen atom, an alkyl, an alkoxy, an optionally substituted alkoxy having 1 to 10 carbon atoms, and an optionally substituted alkoxy-alky.

Formula [I]

$$\text{Au}\left[\begin{array}{c} \end{array}\right]_n$$

19 Claims, 24 Drawing Sheets

Figure 4:
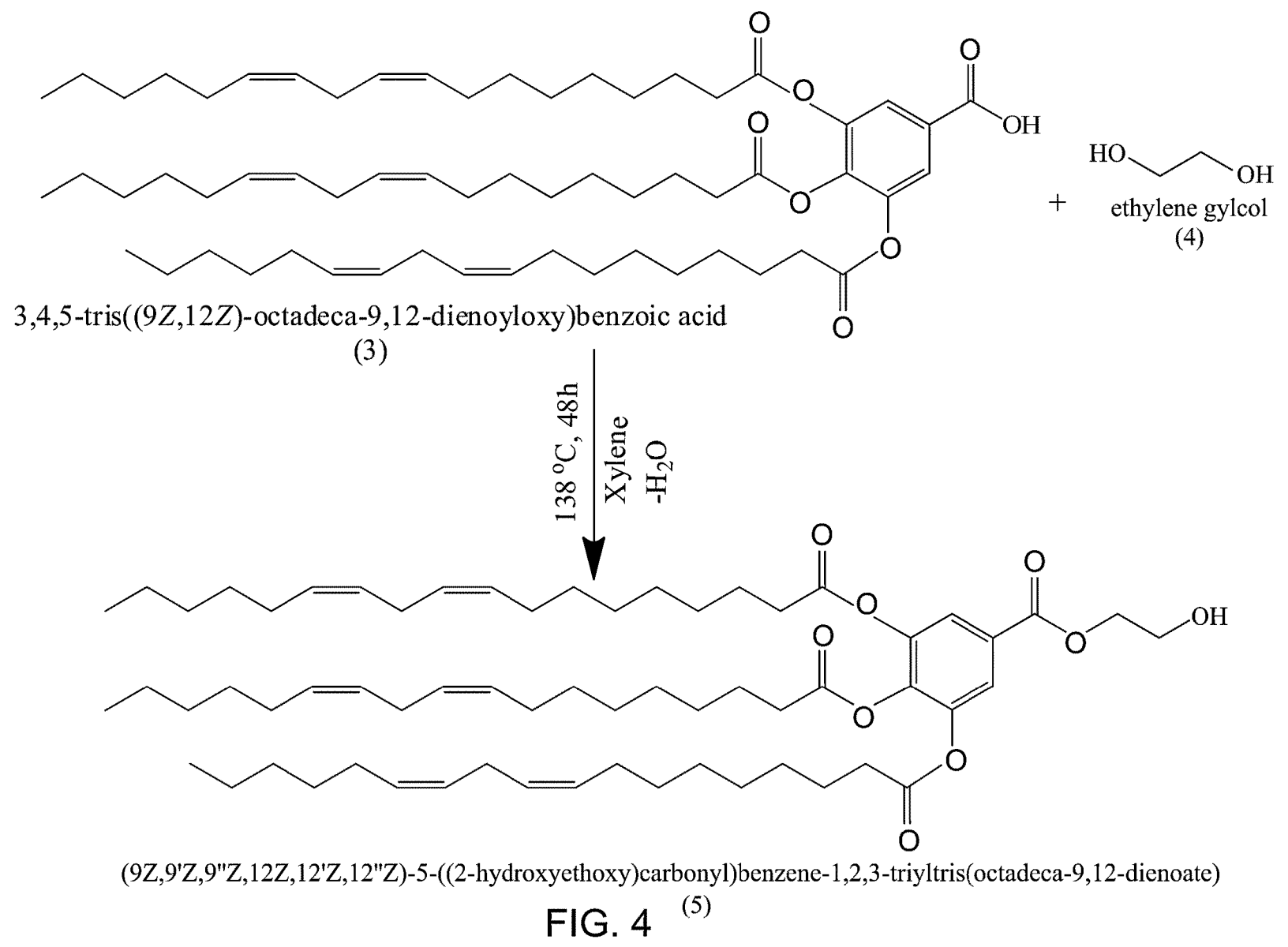

3,4,5-tris((9Z,12Z)-octadeca-9,12-dienoyloxy)benzoic acid
(3)

+ ethylene gylcol
(4)

Xylene
-H₂O
138 °C, 48h (9Z,9'Z,9''Z,12Z,12'Z,12''Z)-5-((2-hydroxyethoxy)carbonyl)benzene-1,2,3-triyltris(octadeca-9,12-dienoate)
(5)

| SEM HV: 30.0 kV | WD: 8.17 mm | 2 μm | VEGA3 TESCAN |
|---|---|---|---|
| View field: 14.1 μm | Det: SE | | |
| SEM MAG: 9.84 kx | Date(m/d/y): 10/25/21 | | Performance in nanospace |

| SEM HV: 30.0 kV | WD: 10.07 mm | ⌊ ⌊ ⌊ ⌊ ⌊ ⌊ ⌊ ⌊ ⌊ ⌊ | VEGA3 |
|---|---|---|---|
| View field: 1.71 µm | Det: SE | 500 nm | TESCAN |
| SEM MAG: 81.0 kx | Date(m/d/y): 10/25/21 | Performance in nanospace | |

| SEM HV: 15.0 kV | WD: 10.06 mm | | VEGA3 |
|---|---|---|---|
| View field: 7.66 µm | Det: SE | 2 µm | TESCAN |
| SEM MAG: 18.1 kx | Date(m/d/y): 10/27/21 | Performance in nanospace | |

| SEM HV: 20.0 kV | WD: 10.17 mm | | VEGA3 TESCAN |
|---|---|---|---|
| View field: 103 µm | Det: SE | 20 µm | |
| SEM MAG: 1.35 kx | Date(m/d/y): 03/09/22 | | Performance in nanospace |

| SEM HV: 20.0 kV | WD: 10.18 mm | ⊔⊔⊔⊔⊔⊔⊔⊔⊔⊔⊔ | VEGA3 TESCAN |
| View field: 102 μm | Det: SE | 20 μm | |
| SEM MAG: 1.36 kx | Date(m/d/y): 03/09/22 | Performance in nanospace | |

| Element | Weight % | MDL | Atomic % | Error % |
|---------|----------|-----|----------|---------|
| O K | 18.7 | 1.06 | 58.8 | 12.7 |
| Na K | 6.5 | 0.90 | 14.2 | 13.8 |
| Cl K | 6.8 | 0.91 | 9.6 | 15.0 |
| Au M | 68.0 | 2.16 | 17.4 | 6.8 |

| Element | Weight % | Auto MDL | Atomic % | Net Int. | Error % |
|---------|----------|----------|----------|----------|---------|
| Na K | 45.2 | 2.20 | 67.3 | 54.8 | 8.5 |
| Cl K | 29.3 | 2.89 | 28.3 | 31.9 | 11.5 |
| Au M | 25.5 | 5.79 | 4.4 | 14.2 | 14.7 |

NANOHYBRID CATALYST FOR HYDROGENATION REACTIONS

STATEMENT REGARDING PRIOR DISCLOSURE BY THE INVENTORS

Aspects of this technology are described in "Synthesis and characterization of gold nanohybrid and its efficiency for benzaldehyde reduction" published in Journal of Molecular Structure, Volume 1289, 2023, 135790, which is incorporated herein by reference in its entirety.

STATEMENT OF ACKNOWLEDGEMENT

This research was supported by Imam Abdulrahman Bin Faisal University (IAU), Kingdom of Saudi Arabia.

BACKGROUND

Technical Field

The present disclosure is directed to a catalyst, and more particularly, to a nanohybrid catalyst, including gold nanohybrid particles, for hydrogenation reactions.

Description of the Related Prior Art

The description of the related prior art provided herein is for the purpose of generally presenting the context of the disclosure. Work of the presently named inventors, to the extent described in this background section, as well as aspects of the description which may not otherwise qualify as prior art at the time of filing, are neither expressly nor impliedly admitted as prior art against the present invention.

Heterogeneous catalysis plays a crucial role in the production of fuels, fertilizers, and fine chemicals. Heterogeneous catalysts offer many advantages over homogeneous catalysts, including easy catalyst separation and reusability. Various methods have been employed to synthesize metal nanoparticles, such as chemical reduction method, sol-gel process, chemical vapor deposition, solvothermal, solution-based synthesis, reverse micelle, and co-precipitation methods. When the size of nanoparticles is decreased to the nanometer scale, the surface-to-volume ratio increases, imparting enhanced catalytic activity. The distinctive electronic and geometric structures of single atoms, nanoclusters, and nanoparticles contribute to their divergent catalytic properties. In particular, the electronic structures of mononuclear metal complexes are heavily influenced by their coordination environments.

Metal nanoparticles with different sizes possess low coordinated corners and edges at the outermost surface layer, which have been identified as active sites. Moreover, a decrease in particle size changes the electronic structure of metal nanoparticles. Thus, it is important to overcome the potential agglomeration of metal nanoparticles by modifying and functionalizing the surfaces of metal nanoparticle. The functionalization of metal nanoparticles is usually based on the interaction established between metal nanoparticle surfaces and branching moieties. According to this, modifications are applied to these branches grafted onto metal nanoparticles to mitigate the tendency for agglomeration. Nanohybrid materials can be considered as a physical composite containing two components—typically inorganic nanoparticles and organic matrix, including organic branches and/or polymer chains.

One promising nanohybrid material involves the integration of inorganic particles at the nanometer or molecular scale into an organic matrix system. Thus, nanohybrids are becoming a field of interest due to their multidisciplinary nature. The intriguing behavior exhibited by these hybrid structures holds great potential across various industrial applications, spanning catalysis, inhibition, oil and water processing, environmental remediation, and even biological systems. Nanohybrids exhibit a diverse array of applications and have found utilization across industries, such as physics, engineering, analytical chemistry life, and medical sciences. Among these applications, metal-based catalysts are a significant class of catalysts commonly used in industry for numerous reactions, including oxidation, dehydrogenation, hydrogenation, hydrotreating, deNOx reactions, ammonia synthesis, and Fischer-Tropsch synthesis.

In these catalysts, the metal constituent is often both expensive and utilized in very small quantities. Smaller metal particles tend to have more active sites exposed compared to larger metallic particles. Henceforward, the size of metal particles emerges as a pivotal structural parameter that influences the catalytic performance of supported metal catalysts. Conventional catalysts contain small metal particles, typically within the nanometer range, dispersed onto a high surface area refractory support.

Gold nanoparticles (AuNPs) are among the earliest nanomaterials to be produced and exploited in a technological application. For instance, gold colloids were used to introduce the dichroic behavior in the famous Lycurgus Cup, which dates to the Romans in the fourth century AD [M. Sankar, Q. He, R. V. Engel, M. A. Sainna, A. J. Logsdail, A. Roldan, D. J. Willock, N. Agarwal, C. J. Kiely, G. J. Hutchings, Role of the support in gold-containing nanoparticles as heterogeneous catalysts, Chem. Rev. 120 (8) (2020) 3890-3938]. Since then, AuNPs and other metal particles have been used to form a range of colors in glassware and windows. Another progress in nanotechnology was the synthesis of stable colloidal AuNPs by Faraday in the mid-19th century [M. X. Faraday, The Bakerian lecture. Experimental relations of gold (and Other Metals) to light, Philos. Trans. R. Soc. Lond. 147 (1857) 145-181].

Despite its long history of use in metallurgy and glass technology, gold was considered to be the archetypal unreactive noble metal, leading to the erroneous assumption that it was unsuitable as a catalyst material. This perception underwent a remarkable shift after Haruta found that supported AuNPs display unparalleled catalytic activity in the realm of low-temperature CO oxidation [M. Haruta, T. Kobayashi, H. Sano, N. Yamada, Novel gold catalysts for the oxidation of carbon-monoxide at a temperature far below 0-degree-C, Chem. Lett. 16 (1987) 405-408]. Hutchings demonstrated that supported gold is the catalyst of choice for producing vinyl chloride monomer via the acetylene hydrochlorination reaction [G. J. Hutchings, Vapor phase hydrochlorination of acetylene: correlation of catalytic activity of supported metal chloride catalysts, J. Catal. 96 (1985) 292-295]. Subsequently, gold catalysis has attracted intense attention from both academic and industrial research communities. It has become clear that the identity of the support material and the gold-support interfacial sites generated often play a crucial role in determining the catalytic behavior of supported AuNPs. In the field of supported metal catalysts, support materials were often considered to be is to provide a method of making the nanohybrid material. Furthermore, a third objective of the present disclosure is to provide a method of benzaldehyde hydrogenation.

SUMMARY

In an exemplary embodiment, a nanohybrid material is described. The nanohybrid material includes a plurality of gold nanohybrid particles having formula (I). In some embodiments, the gold nanohybrid particles have a gold nanoparticle (AuNPs) core and a shell of at least one fatty acid derivative at least partially disposed around the AuNPs core. In some embodiments, the AuNPs core has a square shape and an average particle size of 20 to 60 nanometers (nm). In some embodiments, formula (I) is Formula [I]

inert, and their primary role was to enhance the stability of the small metal particles via anchoring. Many techniques have been reported for the synthesis of AuNPs, including chemical reduction, phase transfer, photochemical reduction, microemulsion, UV-irradiation, gamma-ray irradiation, microwave, electrochemical processes, and ultrasonic methodologies.

With the growing emphasis on environmental considerations, researchers are increasingly embracing the principles of green chemistry. Central to a sustainable synthesis strategy in green chemistry is the use of nontoxic chemical compounds, solvents, and renewable materials. Several eco-friendly techniques have been reported for the formation of AuNPs and other metal nanoparticles. In order to counteract the aggregation of metal nanoparticles, a stabilizing species (or ligand) must be present at surfaces of nanoparticles to prohibit contact between particles. The overall stability of these nanoparticles relies on the effectiveness of two interactions: (i) the interaction between the stabilizer and the nanoparticle surface (inner ligand sphere) and (ii) the interaction between the ligand spheres of adjacent particles (outer ligand sphere). Stabilizers can be classified into three main categories based on their interaction with a metal surface: electrostatic, van der Waals, and covalent stabilizers. The interactions at the inner and outer ligand spheres govern the global stability of these nanoparticles. Thus, modifications and approaches have been reported to stabilize the nanoparticles, including functionalization, capping, grafting, and modification of the metal surfaces.

Although the literature presents a variety of nanohybrid catalysts, there is still a need for a streamlined and effective approach to developing a catalyst capable of both eliminating and overcoming the aforementioned limitations.

In view of the foregoing, it is one objective of the present disclosure to provide a nanohybrid material for hydrogenation reactions. A second objective of the present disclosure In some embodiments, each $R_1$, and $R_2$ are independently selected from the group consisting of a hydrogen atom, and a fatty acid hydrocarbon chain having 16 to 22 carbon atoms. In some embodiments, $R_3$ is selected from the group consisting of a hydrogen atom, an alkyl, an alkoxy, an optionally substituted alkoxy having 1 to 10 carbon atoms, and an optionally substituted alkoxyalky. In some embodiments, n is any positive integer.

In some embodiments, the nanohybrid material has a multi-layered porous structure.

In some embodiments, the multi-layered porous structure of the nanohybrid material has an average layer thickness of 60 to 500 nm.

In some embodiments, the nanohybrid material has a pore size of 1 to 20 micrometers ($\mu$m).

In some embodiments, a weight ratio of the AuNPs core to the fatty acid derivative shell in the nanohybrid material ranges from about 1:10 to 1:50.

In some embodiments, the AuNPs core includes Au nanoparticles having a plurality of carboxylate functional groups. In some embodiments, the at least one fatty acid derivative is connected to a carboxylate functional group of the plurality of carboxylate functional groups of the Au nanoparticles.

In some embodiments, the gold nanohybrid particles are uniformly distributed throughout the nanohybrid material and not forming aggregates.

In some embodiments, the gold nanohybrid particle is (9Z,9'Z,9"Z,12Z,12'Z,12"Z)-5-((2-hydroxyethoxy)carbonyl)benzene-1,2,3-triyl tris(octadeca-9,12-dienoate) (AuNPs/HCBTDE) having formula (II)

Formula [II]

In some embodiments, n is any positive integer.

In some embodiments, a method of making the nanohybrid material includes mixing and dissolving the at least one fatty acid derivative having formula (III) in a first solvent to form a surfactant solution. The method further includes drop-wise adding the surfactant solution into a dispersion containing the AuNPs under continuous agitation to from a reaction mixture containing the nanohybrid material. The method further includes drying the reaction mixture to from the nanohybrid material. In some embodiments, formula (III) is The method further includes preparing the at least one fatty acid derivative of formula (III) by mixing the first product and ethylene glycol in the second solvent in the presence of a sulfonic acid and refluxing to form the at least one fatty acid derivative having formula (III).

In some embodiments, a molar ratio of the fatty acid to the trihydroxybenzoic acid is in a range of 2:1 to 1:2.

In some embodiments, a molar ratio of the first product to the ethylene glycol is in a range of 2:1 to 1:2.

In some embodiments, the fatty acid is octadeca-9,12-dienoic acid.

Formula [III]

In some embodiments, a volume ratio of the surfactant solution to the dispersion is in a range of 1:2 to 1:10.

In some embodiments, the AuNPs present in the dispersion have an average particle size of 30 to 50 nm.

In some embodiments, the method further includes preparing the at least one fatty acid derivative of formula (III) by mixing a fatty acid and a trihydroxybenzoic acid in a second solvent in the presence of a sulfonic acid and refluxing to form a first product having formula (IV)

In some embodiments, the second solvent is xylene. In some embodiments, the sulfonic acid is p-toluene sulfonic acid.

In some embodiments, a method of benzaldehyde hydrogenation is described. The method includes mixing and heating an aromatic aldehyde compound, and the nanohybrid material under a hydrogen flow thereby reducing the aromatic aldehyde compound with hydrogen molecules to form a reduction product. In some embodiments, the reduc- Formula [IV]

tion product is at least one selected from the group consisting of a substituted aromatic alcohol derivative, a substituted aromatic derivative, and an arene.

In some embodiments, up to 80 wt. % of the aromatic aldehyde compound is reduced to form the reduction product at a temperature of 100 to 200° C., each wt. % based on an initial weight of the aromatic aldehyde compound.

In some embodiments, a weight ratio of the nanohybrid material to the aromatic aldehyde compound is in a range of 1:200 to 1:10.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 4 depicts a schematic flowchart for synthesis of (9Z,9'Z,9''Z,12Z,12'Z,12''Z)-5-((2-hydroxyethoxy)carbonyl)benzene-1,2,3-triyl tris(octadeca-9,12-dienoate) (HCBTDE), according to certain embodiments;

FIG. 6A depicts schematic mechanism of 3,4,5-tris(octadecaloxy)benzoic acid and new nonionic surfactants derivatives (HCBTS, HCBTO, and HCBTDE), according to certain embodiments;

DETAILED DESCRIPTION

Figure 1A:
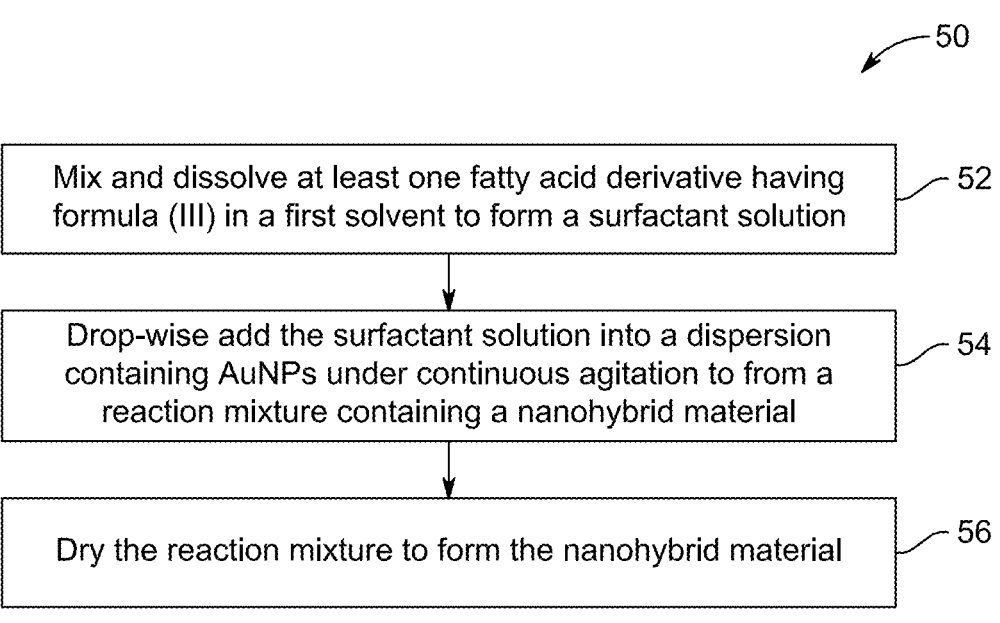
FIG. 1A depicts a schematic diagram of a method of making a nanohybrid material, according to certain embodiments.

When describing the present disclosure, the terms used are to be construed in accordance with the following definitions, unless a context dictates otherwise. Embodiments of the present invention will now be described more fully hereinafter with reference to the accompanying drawings wherever applicable, in which some, but not all embodiments of the disclosure are shown.

Further, as used herein, the use of singular includes plural and the words "a", "an" includes "one" and means "at least one" unless otherwise stated in this application.

Furthermore, the terms "approximately", "approximate", "about," and similar terms generally refer to ranges that include the identified value within a margin of 20%, 10%, or preferably 5%, and any values therebetween.

The use of the terms "include," "includes", "including," "have," "has," or "having" should be generally understood as open-ended and non-limiting unless specifically stated otherwise.

As used herein, the term "substituted" generally refers to at least one hydrogen atom that is replaced with a non-hydrogen group, provided that normal valencies are maintained and that the substitution results in a stable compound. When a group is noted as "optionally substituted", the group may or may not contain non-hydrogen substituents. When present, the substituent(s) may be selected from alkyl, halo (e.g., chloro, bromo, iodo, fluoro), hydroxyl, alkoxy, oxo, alkanoyl, aryloxy, alkanoyloxy, amino (—NH$_2$), alkylamino (—NHalkyl), cycloalkylamino (—NHcycloalkyl), arylamino (—NHaryl), arylalkylamino (—NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkylsulfonyl, arylsulfonyl, arylalkylsulfonyl, sulfonamide (e.g., —SO$_2$NH$_2$), substituted sulfonamide (e.g., —SO$_2$NHalkyl, —SO$_2$NHaryl, —SO$_2$NHarylalkyl, or cases where there are two substituents on one nitrogen selected from alkyl, aryl, or alkylalkyl), nitro, cyano, carboxy, unsubstituted amide (i.e. —CONH$_2$), substituted amide (e.g., —CONHalkyl, —CONHaryl, —CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted and may be either unprotected, or protected as necessary, as known to those skilled in the art.

The term "alkyl", as used herein, unless otherwise specified, generally refers to a straight, branched, or cyclic, saturated aliphatic fragment having 1 to 26 carbon atoms, (e.g., C1, C2, C3, C4, C5, C6, C7, C8, C9, C10, C11, etc.) and specifically includes, but is not limited to, methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, tetradecyl, pentadecyl, hexadecyl, heptadecyl, octadecyl, nonadecyl, eicosyl, guerbet-type alkyl groups (e.g., 2-methylpentyl, 2-ethylhexyl, 2-propylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecyl-

10 lipids or cell wall components and possess, in some cases, striking cosmeceutical, pharmaceutical, and nutraceutical properties.

As used herein, the term "carboxylate functional group" generally refers to carboxyl groups that are a combination of two functional groups attached to a single carbon atom, namely, hydroxyl (single-bonded OH) and carbonyl (double bonded O) groups. The carboxyl (COOH) group is so-named because of the carbonyl group (C=O) and a hydroxyl group. They include carboxylic acids and amino acids.

As used herein, the term "surfactant" generally refers to an organic chemical that, when added to a liquid, changes the properties of that liquid at a surface.

As used herein, the term "aromatic compounds" or "aromatic rings", generally refers to hydrocarbon rings that, by the theory of Hückel, have a cyclic, delocalized $(4n+2)$ pi-electron system. Non-limiting examples of aromatic compounds include benzene, benzene derivatives, compounds having at least one benzene ring in their chemical structure, toluene, ethylbenzene, p-xylene, m-xylene, mesitylene, durene, 2-phenylhexane, biphenyl, phenol, aniline, nitrobenzene, and the like.

In an exemplary embodiment, a nanohybrid material is described. The nanohybrid material includes a plurality of gold nanohybrid particles having formula (I). In some embodiments, formula (I) is Formula [I]

pentadecyl), as well as cyclic alkyl groups (cycloalkyls) such as cyclopropyl, cyclobutyl, cyclopentyl, cyclohexyl, norbornyl, and adamantyl.

The term "optionally substituted alkoxy" generally refers to an alkoxy group which is substituted with one, two, or three substituents independently selected from hydroxyl, alkoxy, carboxy, cyano, alkoxycarbonyl, alkylthio, alkylsulfonyl, halo, haloalkoxy, —CONRR' or —NRR' (where each R is hydrogen, alkyl, hydroxyalkyl, or alkoxyalkyl, and each R' is hydrogen, alkyl, or cycloalkyl) or heterocyclic (preferably heterocycloamino) optionally substituted with one or two groups independently selected from alkyl, hydroxyl, alkoxy, alkylsulfonyl, halo, or —CONRR' where R and R' are as defined above.

As used herein, the term "alkoxy" generally refers to an alkyl group which is singularly bonded to oxygen; thus R—O, where R has C1-C10 carbon atoms.

As used herein, the term "fatty acid derivatives" generally includes, among others, oxylipins, hydroxy fatty acids, diols, alkenones, and wax esters. They can occur as storage in which, each $R_1$, and $R_2$ are independently selected from the group consisting of a hydrogen atom, and a fatty acid hydrocarbon chain having about 16, about 17, about 18, about 19, about 20, and about 21 carbon atoms. Other ranges are also possible. In an embodiment, each $R_1$, and $R_2$ are independently selected from a group of hydrogen atom, and the fatty acid hydrocarbon chain having up to about 22 carbon atoms. $R_3$ is selected from the group consisting of a hydrogen atom, an alkyl, an alkoxy, an optionally substituted alkoxy having 1 to 10 carbon atoms, and an optionally substituted alkoxyalky. In some embodiments, n is any integer. In some preferred embodiments, n is any integer in a range of 5 to 5000, preferably 100 to 4500, preferably 200 to 4000, preferably 300 to 3500, preferably 400 to 3000, preferably 500 to 2500, preferably 600 to 2000, preferably 700 to 1500, or even more preferably 800 to 1000. Other ranges are also possible.

In some embodiments, the gold nanohybrid particle is (9Z, 9'Z, 9"Z, 12Z, 12'Z, 12"Z)-5-((2-hydroxyethoxy)carbonyl)benzene-1,2,3-triyl tris(octadeca-9,12-dienoate) (AuNPs/HCBTDE) having Formula (II).

Formula [II]

In some embodiments, n is any integer. In some preferred embodiments, n is any integer in a range of 5 to 5000, preferably 100 to 4500, preferably 200 to 4000, preferably 300 to 3500, preferably 400 to 3000, preferably 500 to 2500, preferably 600 to 2000, preferably 700 to 1500, or even more preferably 800 to 1000. Other ranges are also possible.

In some embodiments, the gold nanohybrid particles are uniformly distributed throughout the nanohybrid material and are not in the form of aggregates. In some embodiments, the gold nanohybrid particles have a gold nanoparticle (AuNPs) core and a shell of at least one fatty acid derivative at least partially disposed around the AuNPs core. In an embodiment, the AuNPs core is deposited partially or wholly with at least one layer of the shell of at least one fatty acid derivative in a uniform and continuous manner. In some embodiments, at least 70%, at least 80%, at least 90%, or preferably at least 99% of a total surface of the AuNPs core is covered by the shell of at least one fatty acid derivative, based on the total surface area of the shell of at least one fatty acid derivative. Other ranges are also possible. In a preferred embodiment, the shell of at least one fatty acid derivative may form a continuous layer on the AuNPs core. In an embodiment, the shell of at least one fatty acid derivative may form a monolayer on the AuNPs core. In another embodiment, the shell of at least one fatty acid derivative may include more than a single layer on the AuNPs core.

In some embodiments, a weight ratio of the AuNPs core to the fatty acid derivative shell in the nanohybrid material ranges from about 1:1 to 1:100, preferably 1:10 to 1:50, preferably 1:15 to 1:45, preferably 1:20 to 1:40, preferably 1:25 to 1:35, or even more preferably about 1:30. Other ranges are also possible. In some embodiments, the AuNPs core includes Au nanoparticles having a plurality of carboxylate functional groups. In some embodiments, the fatty acid derivative is connected to a carboxylate functional group from among the plurality of carboxylate functional groups of the Au nanoparticles in the core.

Figure 12A:
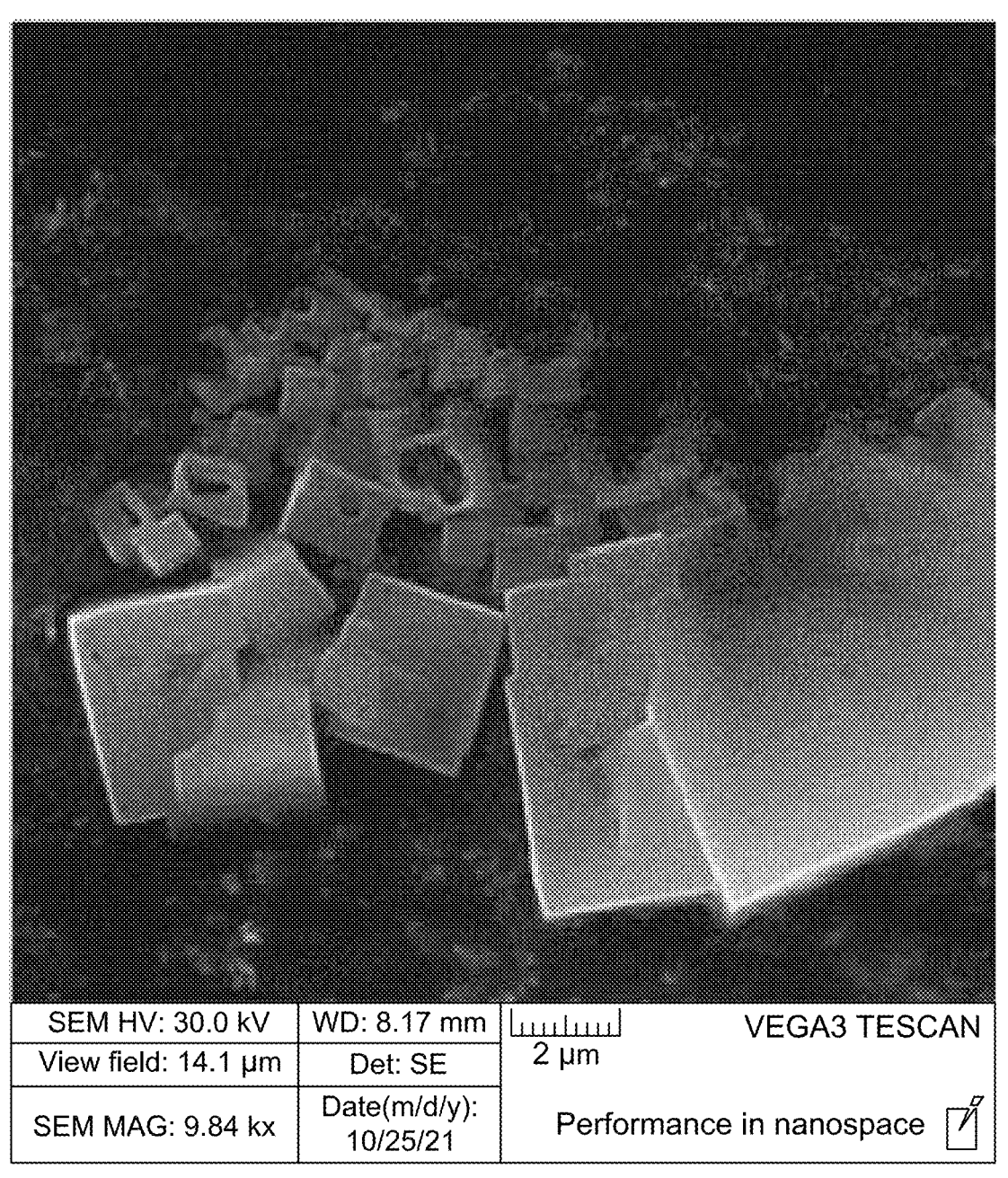
FIG. 12A depicts a scanning electron microscopy (SEM) micrograph of 50 nanometers (nm) AuNPs at 2 micrometers (μm) scale, according to certain embodiments.

In some embodiments, the AuNPs core has one or more faces with a square shape, as depicted in FIG. 12A. The geometry of the AuNPs core may include, but are not limited to, a circular, polygonal, triangular, and rectangular. The AuNPs core preferably has a cuboidal three-dimensional form such as rectangular cuboid, trigonal trapezohedron, trigonal trapezohedron, quadrilateral frustum, parallelepiped, or rhombohedron. In some embodiments, the AuNPs core has an average particle size of 2 to 200 nanometers (nm), preferably 10 to 100 nm, or even more preferably 20 to 80 nm, e.g., based on largest dimension. In some preferred embodiments, the AuNPs core has an average particle size of about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, about 45 nm, about 46 nm, about 47 nm, about 48 nm, about 49 nm, about 50, about 51 nm, about 52 nm, about 53 nm, about 54 nm, about 55 nm, about 56 nm, about 57 nm, about 58 nm, about 59 nm. The AuNPs core has an average particle size up to about 60 nanometers (nm). Other ranges are also possible.

As used herein, the term "energy-dispersive X-ray spectroscopy," or "EDS" generally refers to a material analysis technique to determine the elemental composition of a sample. EDS is often combined with scanning electron microscopy (SEM) and/or transmission electron microscopy (TEM) to provide information about the elements present in a material at a microscopic level.

Figure 13A:
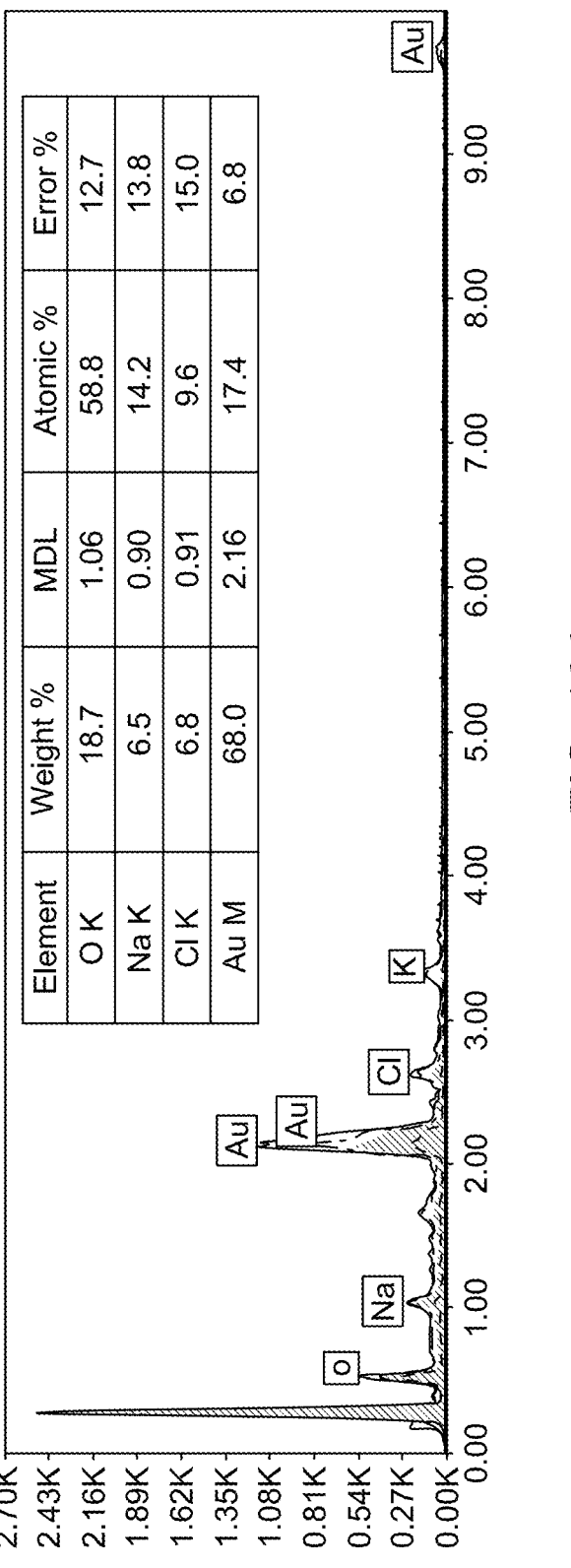
FIG. 13A depicts an energy dispersive spectroscopy (EDS) spectrum of AuNPs 35 nm, according to certain embodiments.

Referring to FIG. 13A, an EDS spectrum of AuNPs with an average particle size of 35 nm. In some embodiments, Au is present in the AuNPs at a concentration of 50 to 80 wt. %, preferably 55 to 75 wt. %, preferably 60 to 70 wt. %, or even more preferably about 68 wt. % based on a total weight of the AuNPs as determined by EDS.

Figure 13B:
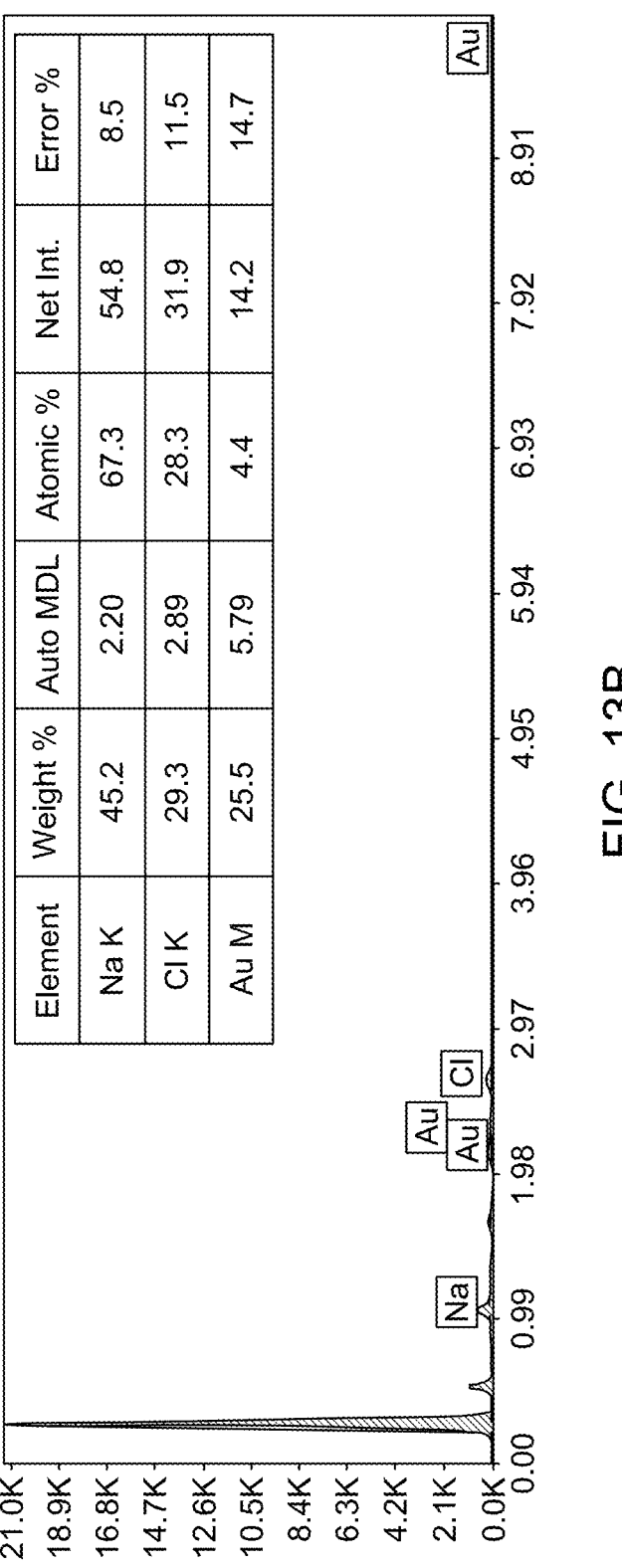
FIG. 13B depicts an EDS spectrum of AuNPs 50 nm, according to certain embodiments.

Referring to FIG. 13B, an EDS spectrum of AuNPs with an average particle size of 50 nm. In some embodiments, Au is present in the AuNPs at a concentration of 15 to 35 wt. %, preferably 20 to 30 wt. %, or even more preferably about 25 wt. % based on a total weight of the AuNPs as determined by EDS.

In some embodiments, the nanohybrid material has a multi-layered porous structure. In some embodiments, the multi-layered porous structure of the nanohybrid material has an average layer thickness of 20 to 1000 nm, or even more preferably 50 to. nm. In some embodiments, the multi-layered porous structure of the nanohybrid material has an average layer thickness of about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, about 200 nm, about 210 nm, about 220 nm, about 230 nm, about 240 nm, about 250 nm, about 260 nm, about 270 nm, about 280 nm, about 290 nm, about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, and about 490 nm. In some preferred embodiments, the multi-layered porous structure of the nanohybrid material has an average layer thickness up to about 500 nm. Other ranges are also possible. In some embodiments, the nanohybrid material has a pore size of about 1 micrometers (μm), about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, and about 19. In some embodiments, the nanohybrid material has a pore size up to about 20 μm. Other ranges are also possible.

FIG. 1A illustrates a flow chart of a method 50 for making the nanohybrid material. The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes mixing and dissolving at least one fatty acid derivative having formula (III) in a first solvent to form a surfactant solution. In some embodiments, formula (III) is In some embodiments, the mixing can be performed via sonication, stirring, swirling, or a combination thereof may be employed to form the surfactant solution. As used herein, the term "sonication" refers to the process in which sound waves are used to agitate particles in a solution.

In some embodiments, the first solvent may include water, an organic solvent, or a mixture thereof. In certain embodiments, the solvent includes water, an alcohol (e.g., methanol, ethanol), or a mixture thereof.

At step 54, the method 50 includes drop-wise adding the surfactant solution into a dispersion containing the AuNPs under continuous agitation to form a reaction mixture containing the nanohybrid material. In certain embodiments, the at least one fatty acid derivative may be added drop-wise into the dispersion in the absence of the first solvent. In some embodiments, the volume ratio of the surfactant solution to the dispersion is in a range of 1:2 to 1:10, preferably 1:3 to 1:9, preferably 1:4 to 1:8, or even more preferably 1:5 to 1:7. Other ranges are also possible. In some embodiments, the AuNPs present in the dispersion have an average particle size of about 30, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, about 45 nm, about 46 nm, about 47 nm, about 48 nm, and about 49 nm. In some embodiments, the AuNPs present in the dispersion have an average particle size of about up to 50 nm. Other ranges are also possible.

At step 56, the method 50 includes drying the reaction mixture to from the nanohybrid material. In some embodiments, the drying of the reaction mixture to from the nanohybrid material can be done by using heating appliances such as ovens, microwaves, autoclaves, hot plates, heating mantles and tapes, oil baths, salt baths, sand baths, air baths, hot-tube furnaces, and hot-air guns. In some embodiments, the drying may be performed at a temperature of 30 to 100° C., preferably 35 to 80° C., preferably 40 to 60° C., or even more preferably about 50° C., for a period time of about 1 to 48 hours, preferably 4 to 36 hours, preferably 8 to 24 hours, or even more preferably about 12 hours. Other ranges are also possible.

Figure 1B:
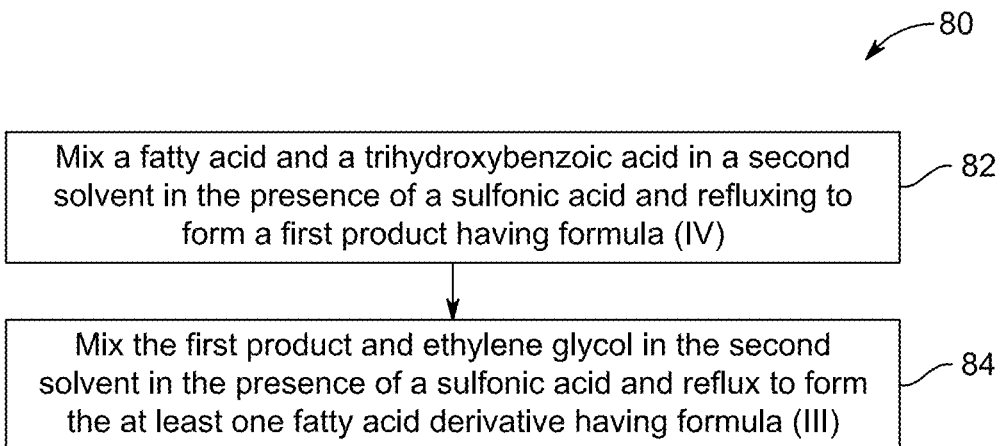
FIG. 1B depicts a schematic diagram of a method of preparing at least one fatty acid derivative of formula (III), according to certain embodiments.

FIG. 1B illustrates a flow chart of a method 80 for preparing the at least one fatty acid derivative of formula (III). The order in which the method 80 is described is not intended to be construed as a limitation, and any number of the described method steps can be combined in any order to implement the method 80. Additionally, individual steps may be removed or skipped from the method 80 without departing from the spirit and scope of the present disclosure.

At step 82, the method 80 includes mixing a fatty acid and a trihydroxybenzoic acid in a second solvent in the presence of a sulfonic acid and refluxing to form a first product having formula (IV).

Formula [III]

Formula [IV]

In some embodiments, the fatty acid is octadeca-9,12-dienoic acid. In some embodiments, the fatty acid may include lauric acid, myristic acid, palmitic acid, palmitoleic acid, stearic acid, oleic acid, linoleic acid, α-linolenic acid, and arachidonic acid. In some embodiments, the second solvent is xylene. In some embodiments, the solvent may include tetrahydrofuran, ethyl acetate, dimethylformamide, acetonitrile, acetone, dimethyl sulfoxide, nitromethane, propylene carbonate, ethanol, formic acid, n-butanol, methanol, acetic acid, water, or any combination thereof. In some embodiments, the sulfonic acid is p-toluene sulfonic acid. In some embodiments, a molar ratio of the fatty acid to the trihydroxybenzoic acid is in a range of 10:1 to 1:10, preferably 5:1 to 1:5, preferably 2:1 to 1:2, or even more preferably 1:1. Other ranges are also possible.

At step 82, the method 80 includes mixing the first product and ethylene glycol in the second solvent in the presence of a sulfonic acid and refluxing to form the at least one fatty acid derivative having formula (III). In some embodiments, a molar ratio of the first product to the ethylene glycol is in a range of 10:1 to 1:10, preferably 5:1 to 1:5, preferably 2:1 to 1:2, or even more preferably 1:1. Other ranges are also possible. In some embodiments, the refluxing may be performed at a temperature of about 120 to 180° C., preferably 130 to 160° C., or even more preferably about 138° C. for at least 12 hours, preferably at least 24 hours, or even more preferably at least 48 hours. Other ranges are also possible.

According to an aspect of the present disclosure, a method for benzaldehyde compound hydrogenation is described. The method includes mixing and heating an aromatic aldehyde compound, and the nanohybrid material under a hydrogen flow thereby reducing the aromatic aldehyde compound with hydrogen molecules to form a reduction product. In some embodiments, a weight ratio of the nanohybrid material to the aromatic aldehyde compound is in a range of 1:200 to 1:10, preferably 1:150 to 1:20, preferably 1:100 to 1:30, or even more preferably about 1:50. Other ranges are also possible. In some embodiments, the reduction product is at least one selected from the group consisting of a substituted aromatic alcohol derivative, a substituted aromatic derivative, and an arene. In some preferred embodiments, at least 50 wt. %, preferably at least 60 wt. %, or even more preferably at least 70 wt. % of the aromatic aldehyde compound is reduced to form the reduction product at a temperature of about 100° C., 110° C., 120° C., 130° C., 140° C., 150° C., 160° C., 170° C., 180° C., 190° C., more preferably 138° C., each wt. % based on an initial weight of the aromatic aldehyde compound. Other ranges are also possible. In some preferred embodiments, up to 60 wt. %, preferably up to 80 wt. %, or even more preferably up to 90 wt. % of the aromatic aldehyde compound is reduced to form the reduction product at a temperature of about 100° C., 110° C., 120° C., 130° C., 140° C., 150° C., 160° C., 170° C., 180° C., 190° C., more preferably 138° C., each wt. % based on the initial weight of the aromatic aldehyde compound. Other ranges are also possible. In some preferred embodiments, up to 80 wt. % of the aromatic aldehyde compound is reduced to form the reduction product at a temperature of about up to 200° C. each wt. % based on an initial weight of the aromatic aldehyde compound.

In some embodiments, the aromatic aldehyde compound is benzaldehyde. The hydrogenation is performed at a temperature of 100 to 200° C. at a pressure of 1 to 250 torr, preferably 5 to 200 torr for a period of time in a range of 1 to 48 hours, or preferably 24 hours to achieve a conversation of 20 to 85% based on a total initial weight of the benzaldehyde. In some embodiments, the product after the reduction may include about 5 to 90 wt. % benzyl alcohol, 1 to 20 wt. % toluene, and 5 to 95 wt. % benzene, each wt. % based on a total weight of the product after the reduction. In a preferred embodiments, the product includes about 80 to 90% benzyl alcohol, or even more preferably 82 to 88%, based on the total weight of the product after the reduction. Other ranges are also possible.

The structures of the citric acid-based additive may be characterized by Fourier transforms infrared spectroscopy (FT-IR). In some embodiments, the FT-IR may be collected in a Nicolet 6700 Thermo Scientific instrument acquired in a range of 4000 to 400 centimeter inverse $(cm^{-1})$ at 4 $cm^{-1}$ resolution. 20 scans were carried out for each sample.

Figure 6A:
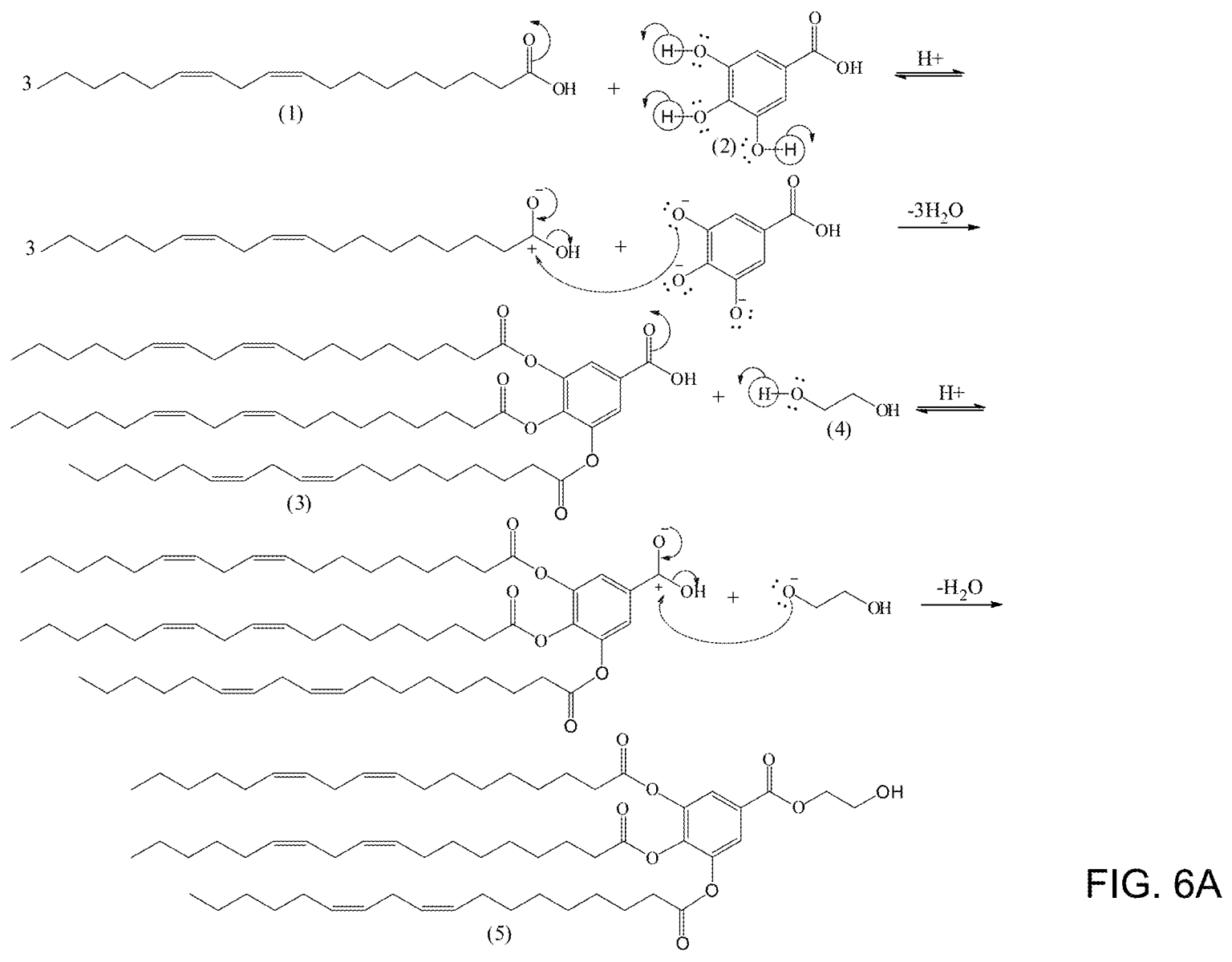
Figure 6B:
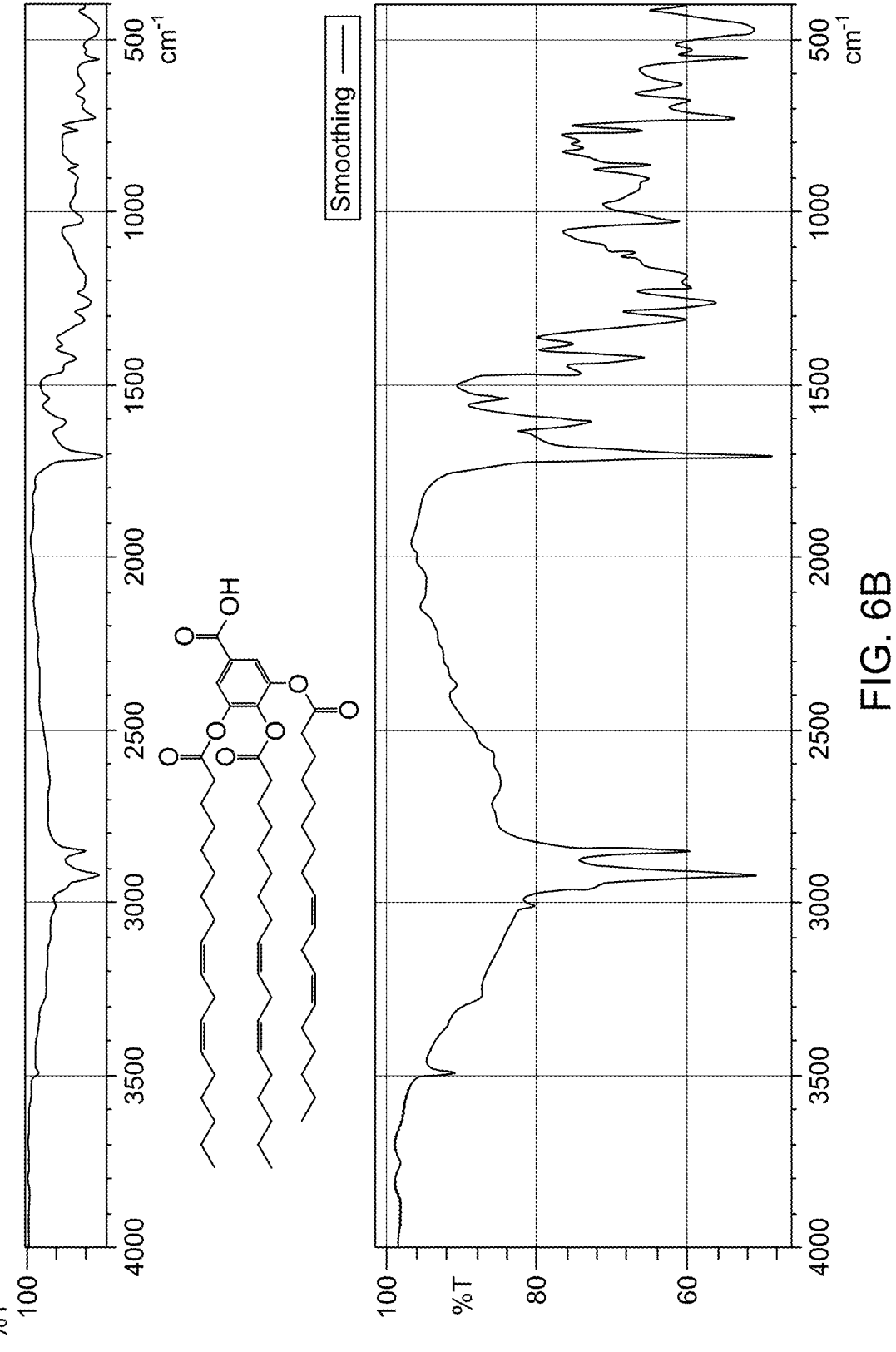
FIG. 6B depicts Infrared (IR) spectrum of ODEBA, according to certain embodiments.

In some embodiments, ODEBA of formula (IV) has peaks at about 1200 $cm^{-1}$, about 1430 $cm^{-1}$, about 1614 $cm^{-1}$, about 1710 $cm^{-1}$, and 2800 to 3300 $cm^{-1}$ in a Fourier transform infrared spectrum (FT-IR), as depicted in FIG. 6B.

Figure 9:
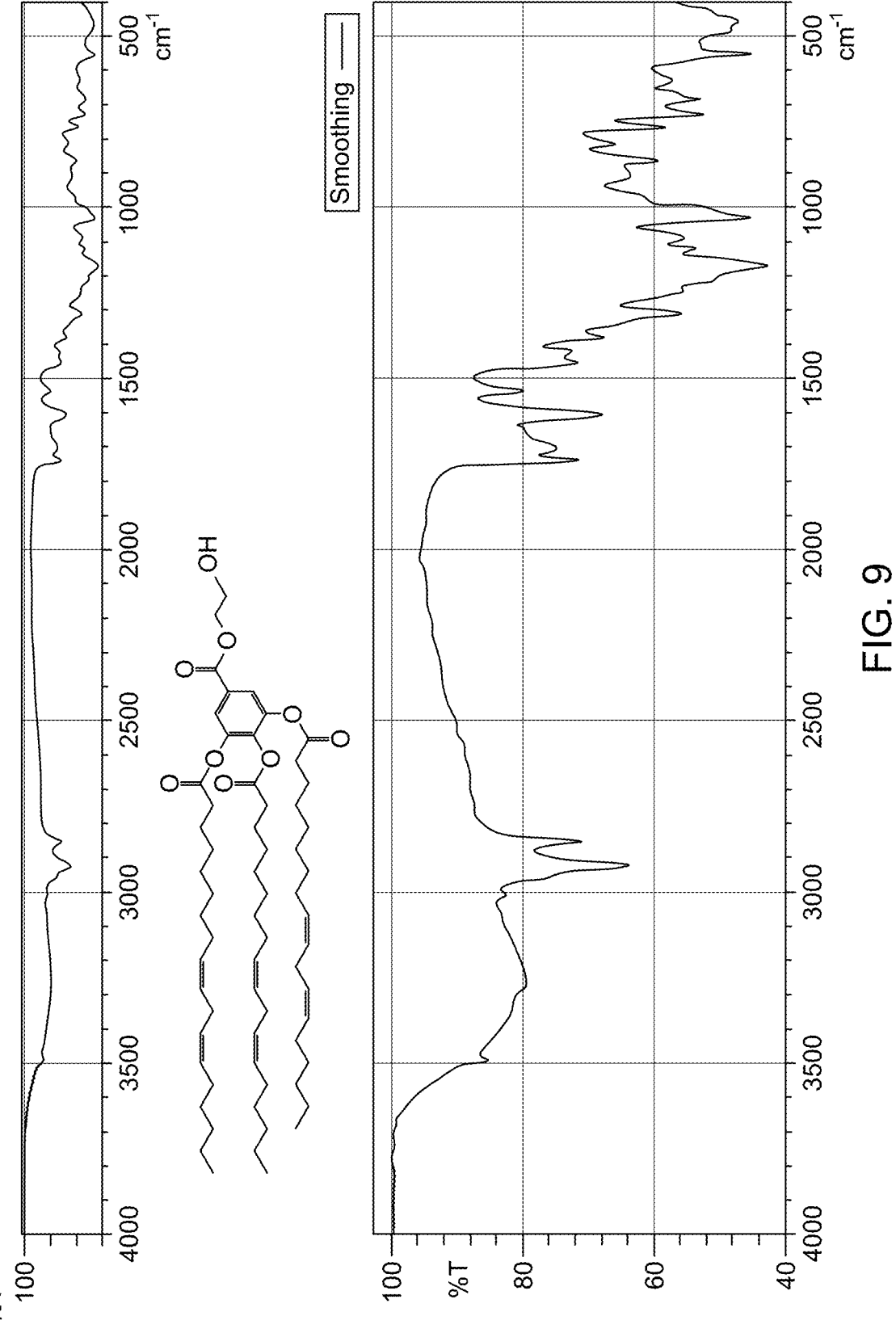
FIG. 9 depicts IR of HCBTDE, according to certain embodiments.

In some embodiments, HCBTDE of formula (III) has peaks at about 1179 $cm^{-1}$, about 1534 $cm^{-1}$, about 1737 $cm^{-1}$, and 3000 to 3350 $cm^{-1}$ in the Fourier transform infrared spectrum (FT-IR), as depicted in FIG. 9.

$^1H$ and $^{13}C$ NMR spectra may be recorded on a 500 MHz spectrometer (Bruker spectrometer) using the residual DMSO-$d_6$ at δ 2.50 ppm and $^{13}C$ DMSO-$d_6$ signal at δ 39.52 ppm as internal standards.

Figure 7:
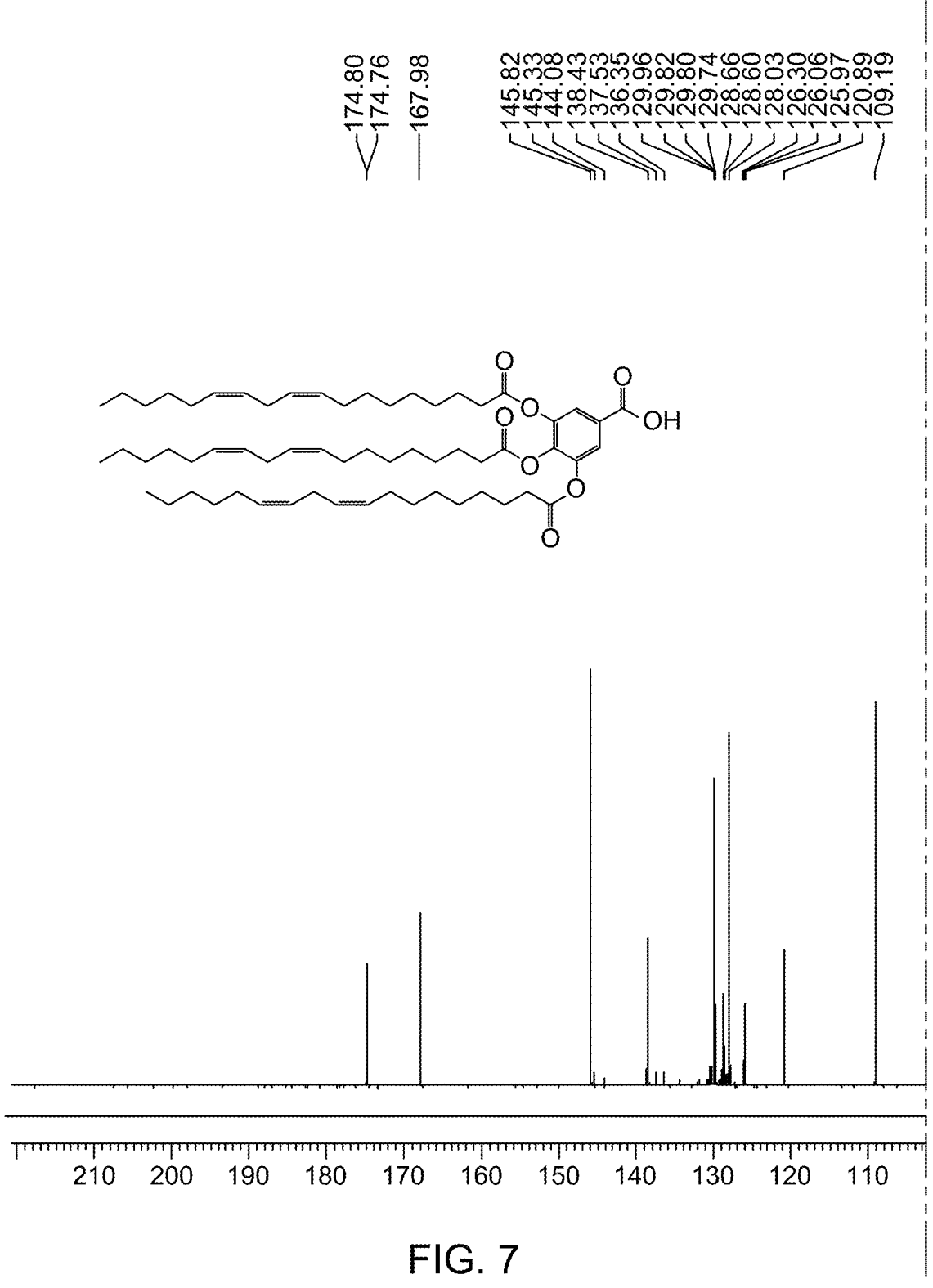
FIG. 7 depicts $^{13}$C nuclear magnetic resonance (NMR) spectrum (500 megahertz (MHz)) of ODEBA in DMSO at 25° C., according to certain embodiments.
Figure 7:
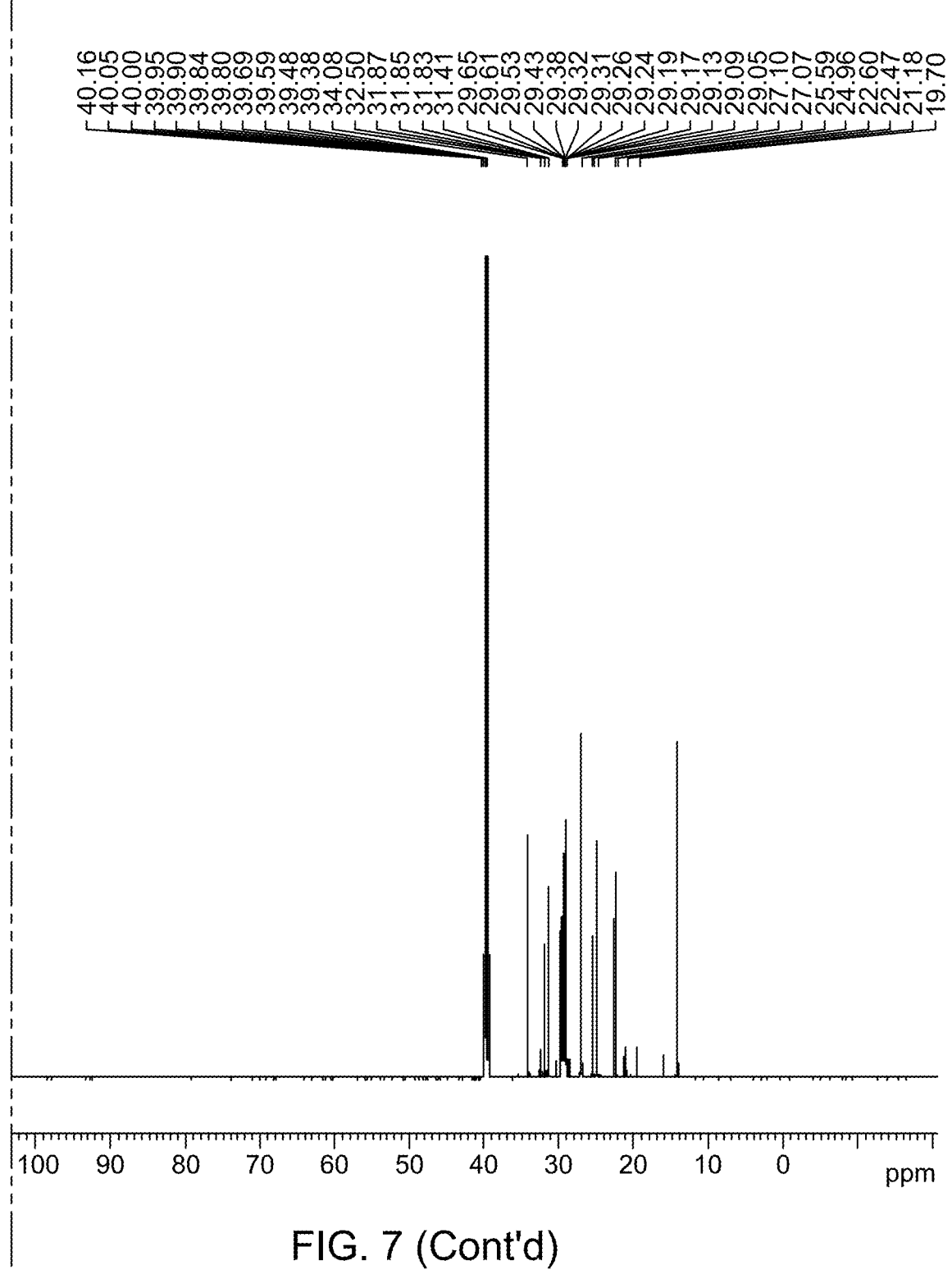

Referring to FIG. 7, $^{13}C$ NMR spectra of ODEBA of formula (IV) in DMSO-$d_6$. In some embodiments, the ODEBA of formula (IV) has peaks in a range of 10 to 180, or more preferably about 14.1, about 22.6, about 24.9, about 25.6, about 27.1, about 29.0-29.6, about 31.8, about 34.0, about 109.1-145.8, about 128.0, about 129.9, about 167.9, and about 174.8, as depicted in FIG. 7. Other ranges are also possible.

Figure 8:
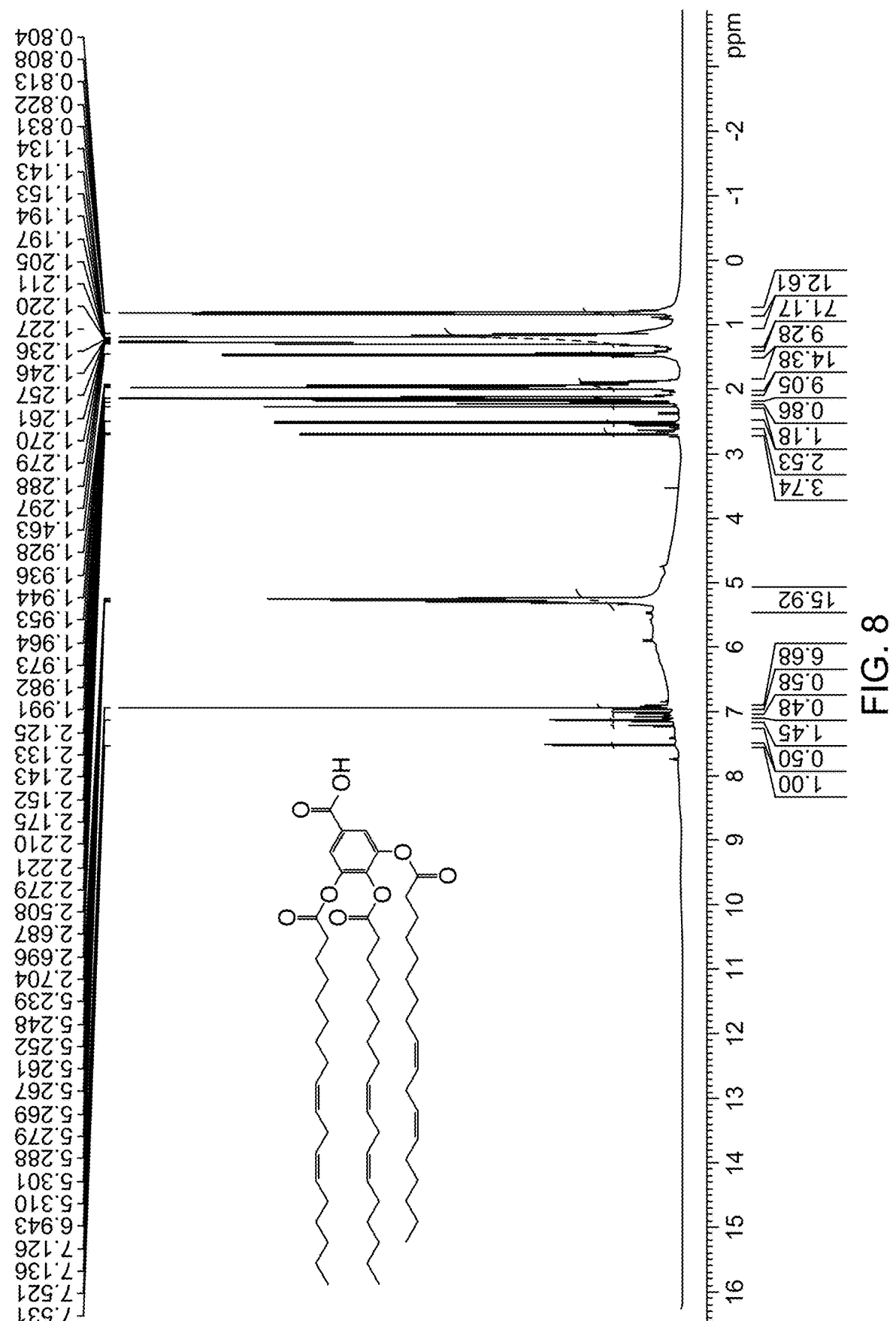
FIG. 8 depicts $^1$H NMR spectrum (500 MHz) of ODEBA in DMSO at 25° C., according to certain embodiments.

Referring to FIG. 8, $^1H$ NMR spectra of the ODEBA of formula (IV) in DMSO-$d_6$. In some embodiments, the ODEBA of formula (IV) has peaks in a range of 0.5 to 8, or more preferably about 0.83, about 1.13-1.29, about 1.46, about 1.99, about 2.14, about 2.70, about 5.26-5.47, and about 6.91-7.53, as depicted in FIG. 8. Other ranges are also possible.

Figure 11:
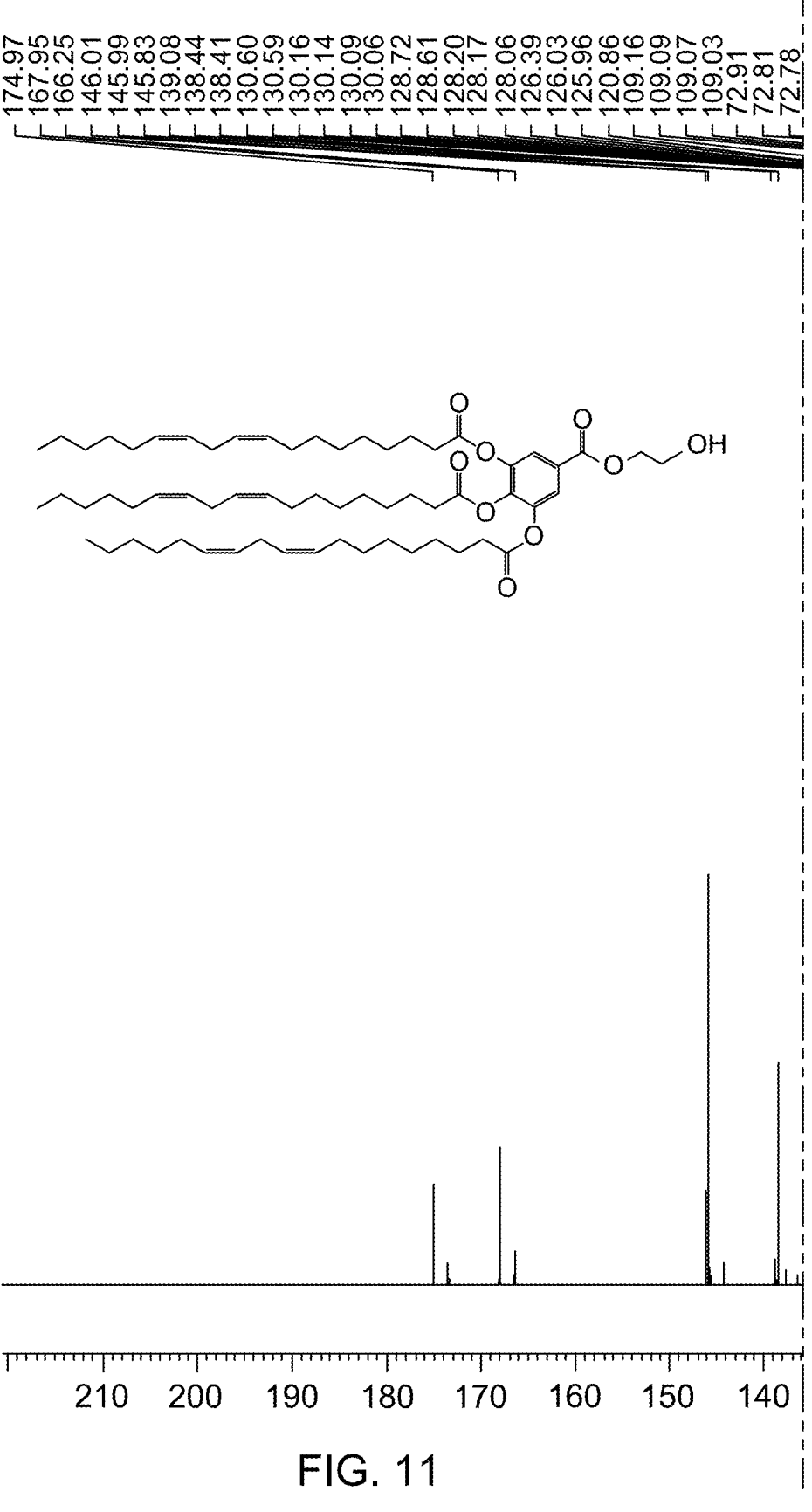
FIG. 11 depicts $^{13}$C NMR Spectrum (500 MHz) of HCBTDE in DMSO at 25° C., according to certain embodiments.
Figure 11:
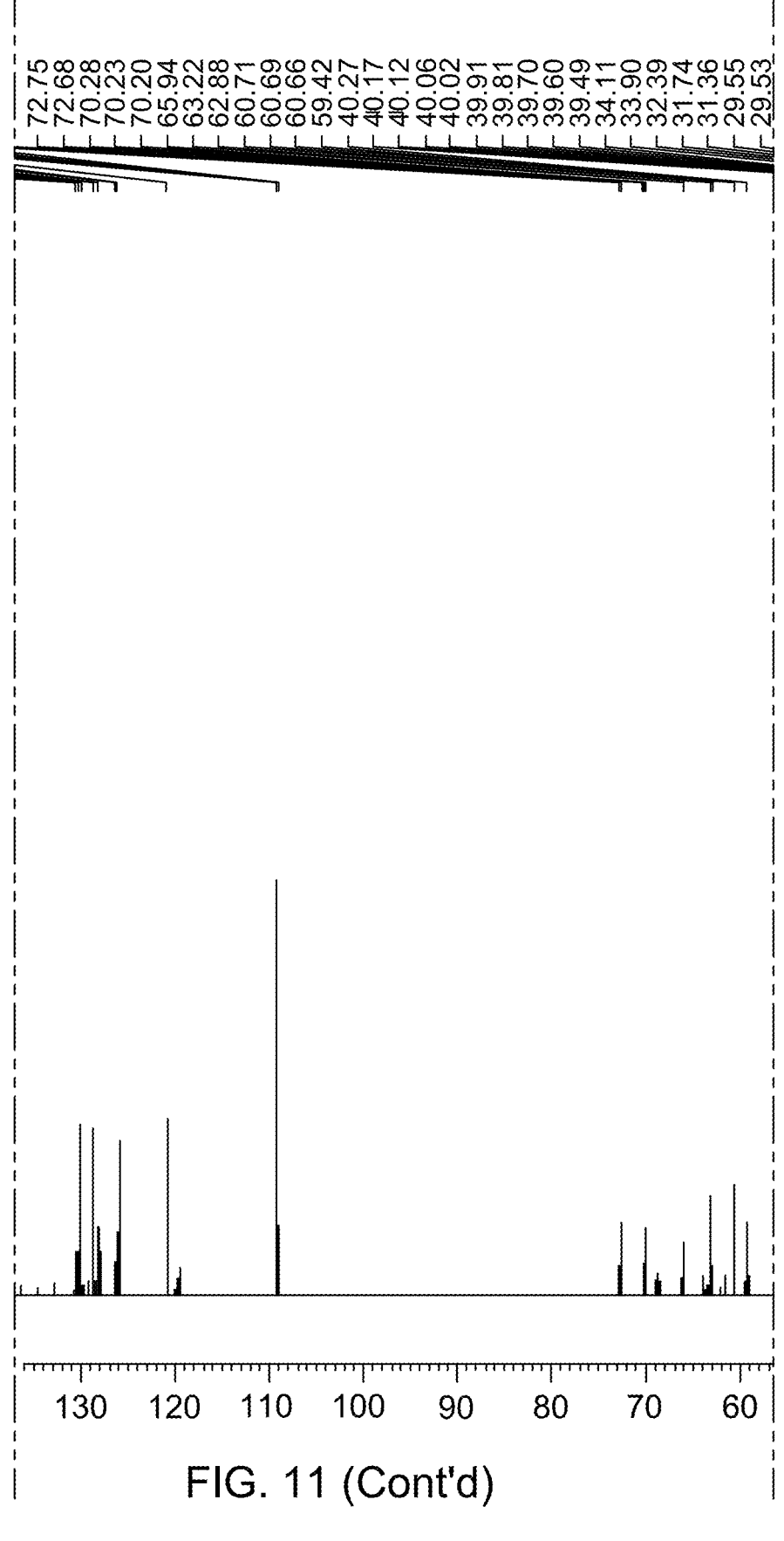
Figure 11:
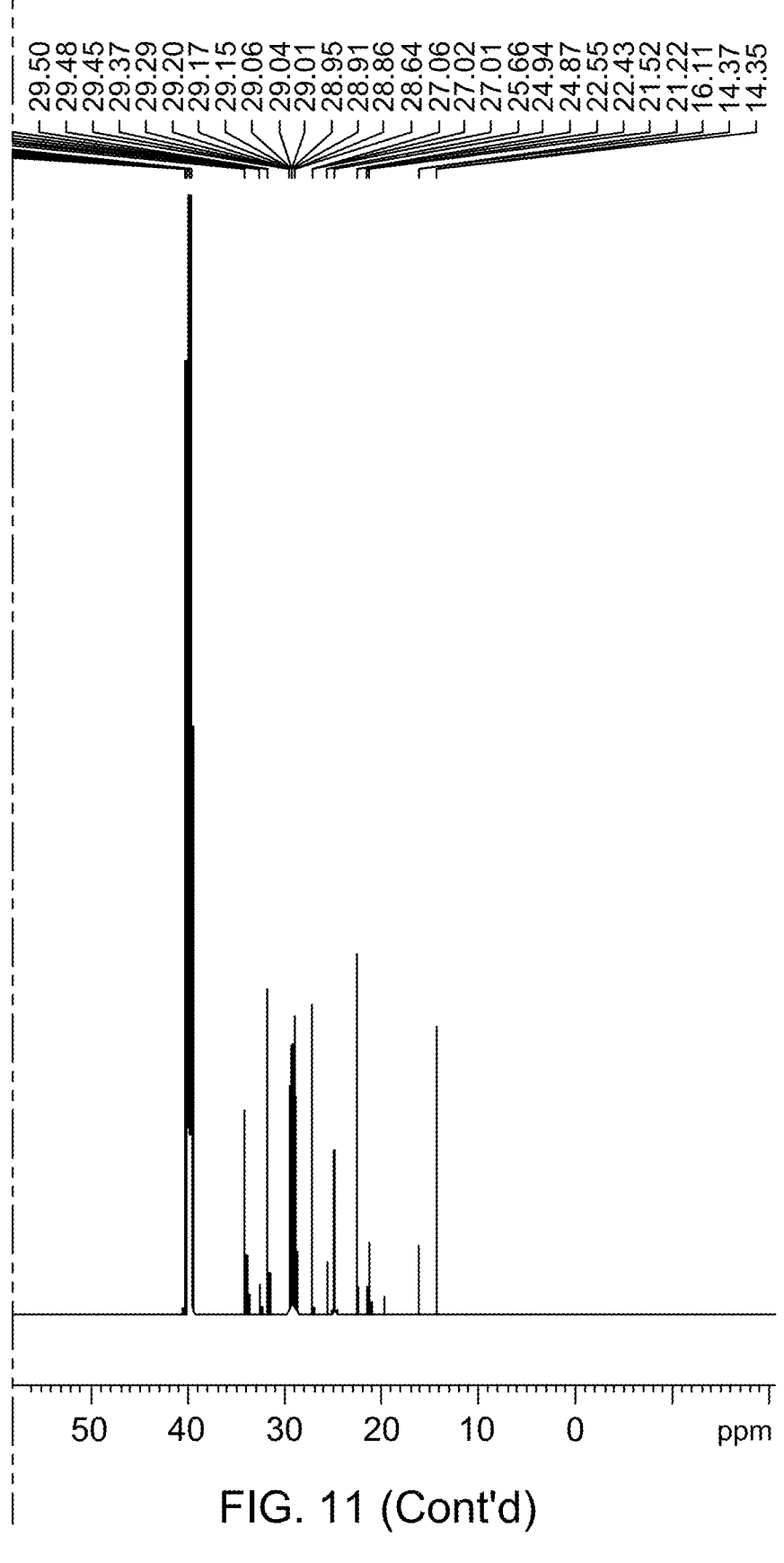

Referring to FIG. 11, $^{13}$C NMR spectra of HCBTDE of formula (III) in DMSO-d$_6$. In some embodiments, the HCBTDE of formula (III) has peaks in a range of 10 to 180, or more preferably about 14.3, about 25.6, about 27.0, about 31.7, about 34.1, about 60.7, about 66.3, about 109-146.0, about 128.0, about 130.6, about 167.9, and about 175.0, as depicted in FIG. 11. Other ranges are also possible.

Figure 10:
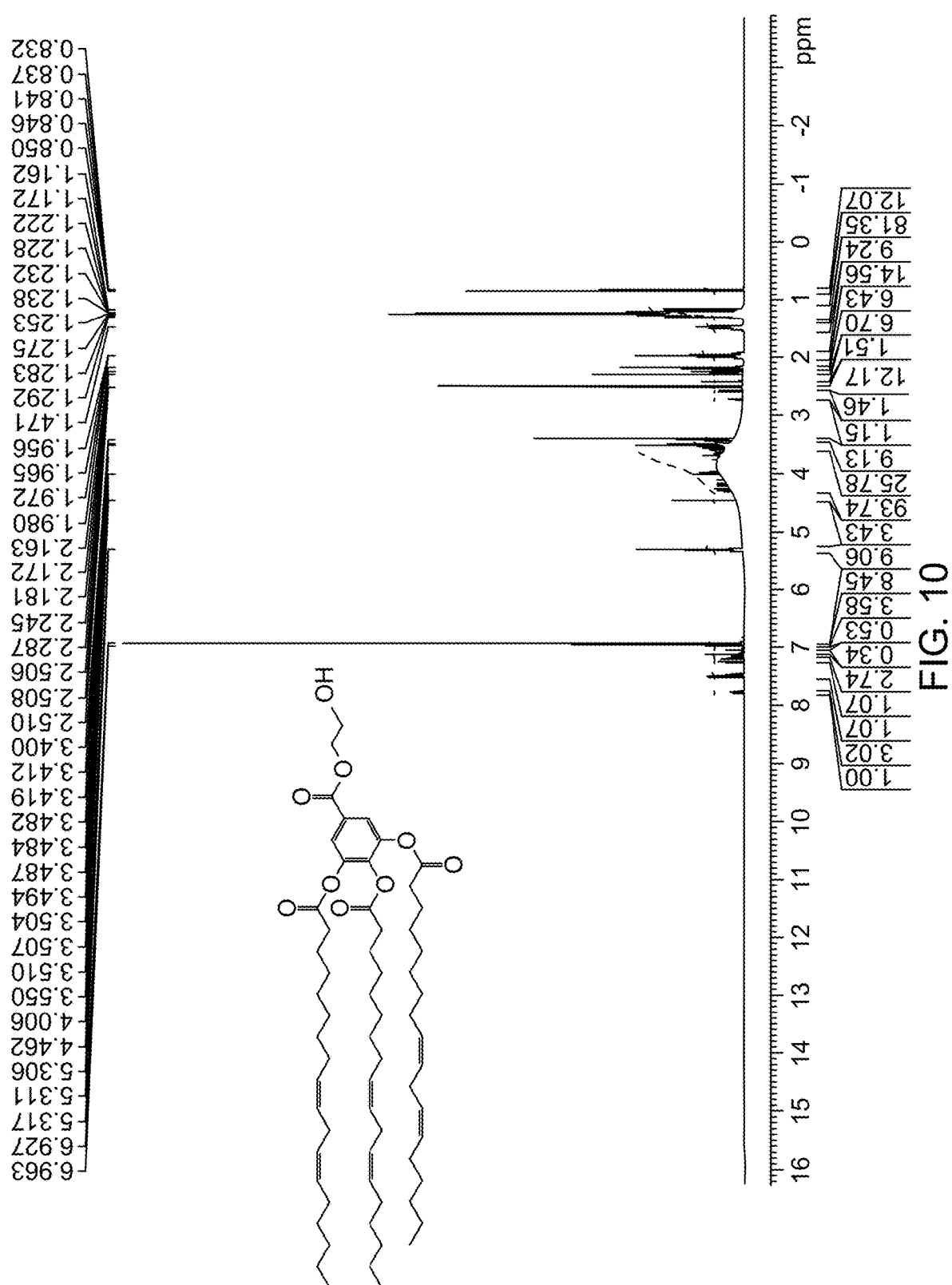
FIG. 10 depicts $^1$H NMR spectrum (500 MHz) of HCBTDE in DMSO at 25° C., according to certain embodiments.

Referring to FIG. 10, $^1$H NMR spectra of the HCBTDE of formula (III) in DMSO-d$_6$. In some embodiments, the HCBTDE of formula (III) has peaks in a range of 0.5 to 8, or more preferably about 0.85, about 1.15-1.29, about 2.17, about 3.41, about 3.51, about 4.46, about 5.31, and about 6.91-7.78, as depicted in FIG. 10. Other ranges are also possible.

As used herein, the term "ultraviolet-visible spectroscopy," or "UV-Vis" generally refers to an analytical technique for examining the interaction of light with matter in the ultraviolet (UV) and visible (Vis) regions of the electromagnetic spectrum. In the present disclosure, the UV-Vis measurements of AuNPs solution and nanohybrid derivatives were performed on an 8UVD11064, (Somatko) spectrophotometer in a 1 cm pathlength quartz cuvette.

Figure 14:
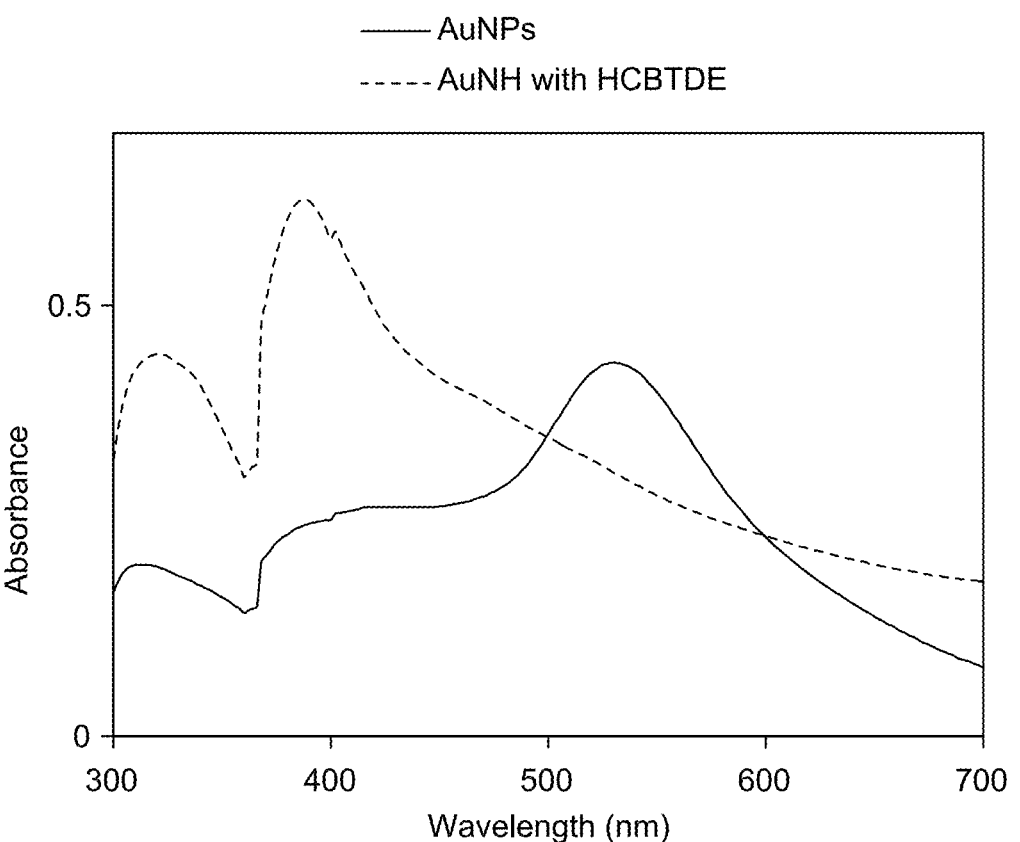
FIG. 14 depicts an ultraviolet (UV) spectra of prepared AuNPs with and without the addition of nonionic surfactant AuNPs/HCBTDE, according to certain embodiments.

Referring to FIG. 14, the UV spectrum of the synthesized gold nanoparticles with and without the addition of nonionic surfactant HCBTDE. In some embodiments, the AuNPs has peaks in a range of about 300 to 380 nm, or even more preferably about 320 nm; and about 380 to 450 nm, or even more preferably about 400 nm. In some preferred embodiments, the nanohybrid material of formula (II) (AuNPs with HCBTDE) has peaks in a range of 300 to 380 nm, or even more preferably about 310 nm; and about 500 to 600 nm, or even more preferably about 530 nm. Other ranges are also possible.

EXAMPLES

The following examples demonstrate a nanohybrid material described herein. The examples are provided solely for illustration and are not to be construed as limitations of the present disclosure, as many variations thereof are possible without departing from the spirit and scope of the present disclosure.

Example 1: Materials and Methods

All glassware used in preparing the samples was washed with soap, tap water, acetone, and distilled water, and then dried in an oven at 70° C. The experiment was installed using the Dean-Stark apparatus and the condenser under the fume hood. All samples were prepared in a clean atmosphere and under an oil bath at 138° C. Dean-Stark apparatus, oil bath, water bath, sensitive balance, hose water, heating magnetic stirrer, and rotary evaporator equipment were used. All chemicals may be obtained from Sigma-Aldrich (St Louis Mo, USA): hydrogen tetrachloroaurate (iii) trihydrate (HAuCl$_4$·3H$_2$O), gallic acid, p-toluene sulphonic acid, octadeca-9,12-dienoic acid (0.005 mol), xylene, ethylene glycol, petroleum ether, ethyl acetoacetate, cyclohexane, acetone, paraffin liquid heavy, silver nitrate, trisodium citrate.

The UV-Vis measurements of AuNPs solution and nanohybrid derivatives prepared were examined by spectrophotometer (manufactured by Somatko, 8UVD11064, 2013)

using a 1-centimeter (cm) pathlength quartz cuvette. FT-IR spectra measurements were performed on prepared samples from (SHIMADZU, 206-31010-85, Kyoto, Japan). $^1$H nuclear magnetic resonance (NMR) and $^{13}$C NMR were recorded on Bruker spectrometer (manufactured by Bruker, Billerica, Massachusetts, United States), 850 and 500 MHz. The samples were prepared by dissolution of 0.5 milliliters (ml) of sample in 0.6 ml of dimethyl sulfoxide (DMSO). Chemical shifts (δ) are presented in part per million (ppm) using tetramethyl silane (TMS) as an internal standard. GCMS of FAME were recorded on a mass hunter acquisition SW, GC/MS acquisition, equilibrium time 0.5 min max temperature 325° C., oven program 50° C. for 1 min, pressure 22.231 psi, total flow 34.223 milliliters per minute (ml/min). Septum purge flow 3 ml/min, injection pulse pressure 40 psi unit, 0.2 min.

Example 2: Synthesis of Gold Nanoparticles (AuNPs)

0.01 grams (gm) of hydrogen tetrachloroaurate (III) trihydrate (HAuCl$_4$·3H$_2$O) was dissolved in 100 ml of distilled water and then placed in an oil bath (at 90° C. to prepare 50 nm AuNPs and at 70° C. to prepare 35-30 nm AuNPs) for 30 min with stirring using stirrer bar. The solution was prepared and then taken with a 500 millimeters (mm) pipette (5 time until reaching 100 Mm). Then 0.1 g of trisodium citrate Na$_3$C$_6$H$_5$O$_7$ was prepared in 100 ml of distilled water and added to the gold bottle in the hot plate (5 time until reaching 100 Mm) gradually at the same time; it was heated (at 90° C. to prepare 50 nm AuNPs, and at 70° C. to prepare 35-30 nm AuNPs) for 30 min with continuous stirring using stirrer bar, and then transferred to the fridge.

Example 3: Synthesis of New Gold Nanohybrid Derivatives

The nanohybrid derivatives may be prepared in three steps:

Step 1: Synthesis of 3,4,5-Tris((9Z,12Z)-Octadeca-9,12-Dienoyloxy) Benzoic Acid (ODEBA)

Figure 2:
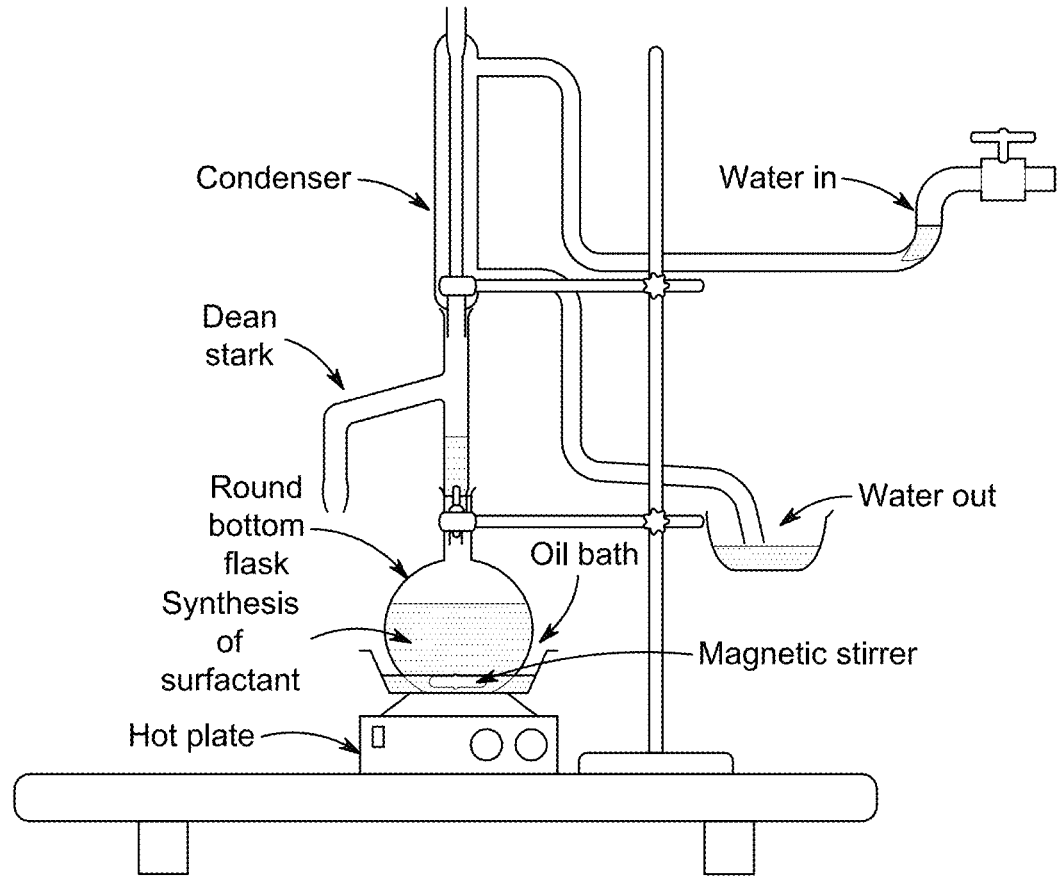
FIG. 2 depicts an experimental setup for the preparation of surfactants of formula (I), according to certain embodiments.
Figure 3:
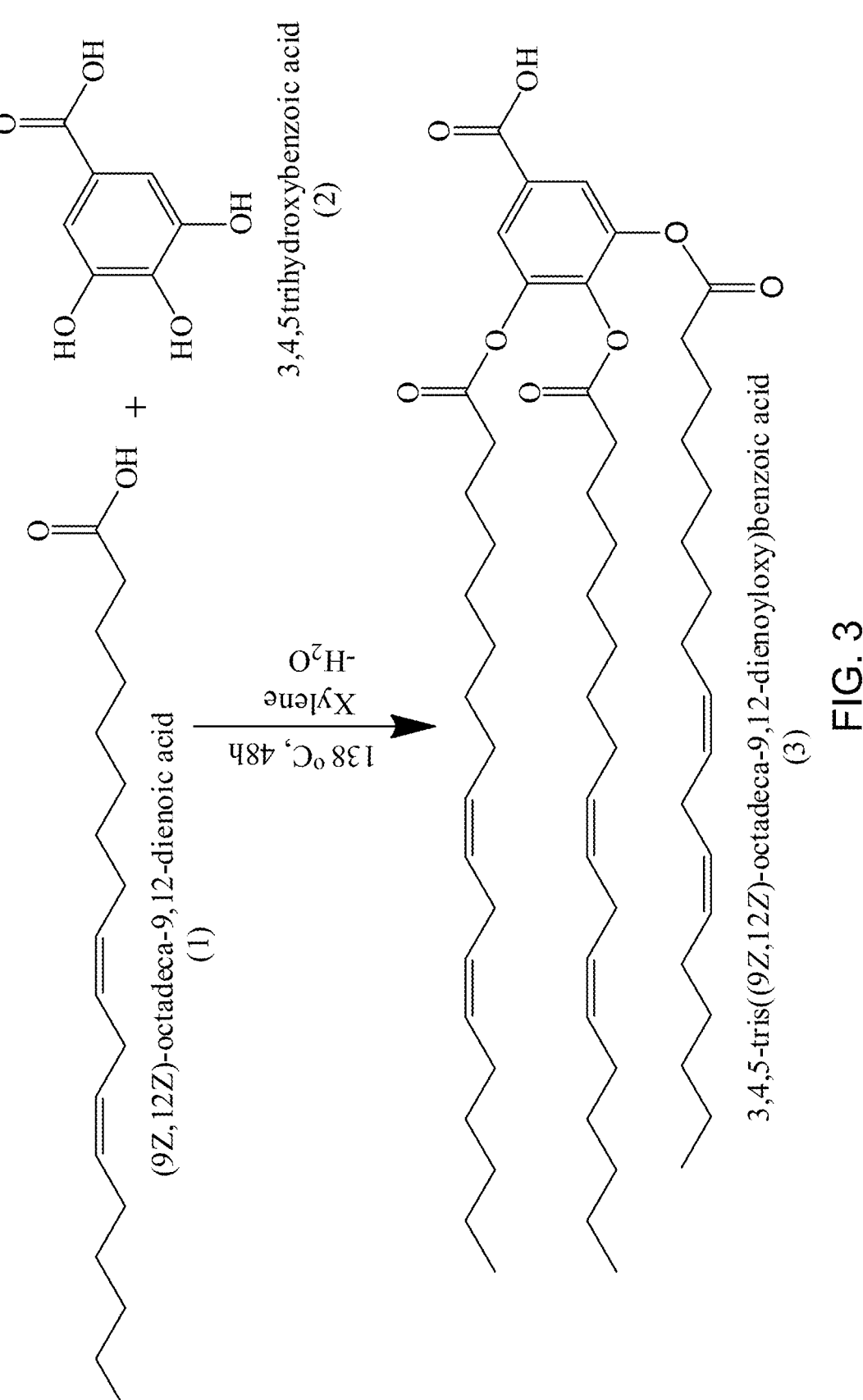
FIG. 3 depicts a schematic flowchart for the synthesis of 3,4,5-tris((9Z, 12Z)-octadeca-9,12-dienoyloxy)benzoic acid (ODEBA), according to certain embodiments.

The experiment was installed as shown in FIG. 2 and FIG. 3. Octadeca-9,12-dienoic acid (0.005 mol), 3,4,5-trihydroxybenzoic acid (gallic acid) (0.005 mol) were weighed and added into a 250 milliliters (mL) round bottom flask followed by addition xylene (20 ml) as a solvent and p-toluene sulfonic acid (0.01%) as a catalyst to obtain a mixture. The mixture was stirred with a magnetic stirrer, and then placed in an oil bath in a heating magnetic stirrer. The reaction mixture was refluxed at 138° C. for 48 h until the water of the reaction (0.005 mol, 0.09 ml) was removed in the Dean-Stark apparatus. The product was washed with petroleum ether to extract the catalyst. The solvent was removed using a vacuum rotary evaporator (manufactured by BUCHI Labortechnik AG, Flawil, Switzerland, 2019).

Step 2: Synthesis of New Nonionic Surfactant (9Z, 9'Z,9"Z,12Z,12'Z,12"Z)-5-((2-hydroxyethoxy)carbonyl)benzene-1,2,3-triyl tris(octadeca-9,12-dienoate) (HCBTDE)

0.005 mol of the compound prepared in step 1 (ODEBA) was weighed and then individually esterified with 0.005 mol of ethylene glycol in a 250 mL round bottom flask, followed by the addition of xylene (20 ml) as a solvent and p-toluene sulfonic acid (0.01%) as a catalyst to obtain a mixture. The mixture was stirred with a magnetic stirrer. The reaction mixture was refluxed at 138° C. for 10 h until the water of the reaction (0.005 mol, 0.09 ml) was removed in the Dean-Stark apparatus. Then the product was washed with petroleum ether to extract the catalyst, and the solvent was removed using a vacuum rotary evaporator (BUCHI Labortechnik AG, 2019).

Step 3: Synthesis of New Gold Nanohybrid with Nonionic Surfactant AuNPs/HCBTDE)

Figure 5:
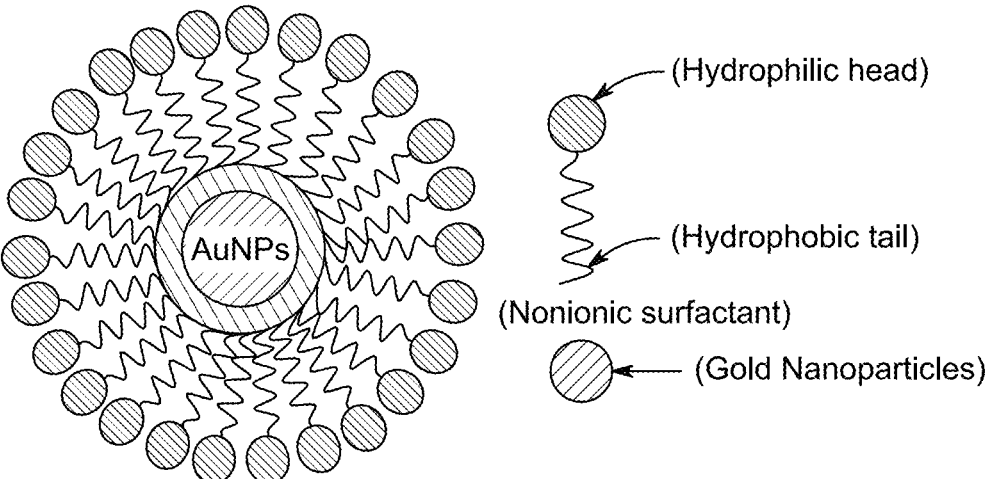
FIG. 5 depicts synthesis of gold nanohybrids (AuNPs/HCBTDE), according to certain embodiments.

5 mL of the surfactant solution from step 2 (HCBTDE) was added to 20 mL of the prepared AuNPs drop-by-drop for 20 minutes. The mixture was stirred continuously for 24 hours until the color changed, then the product was removed from the solvent (water) using a vacuum rotary evaporator (BUCHI Labortechnik AG, 2019) to obtain the nanohybrid (AuNPs/HCBTDE) surfactants. The gold nanohybrid material prepared by the method of present disclosure (AuNPs/HCBTDE) is depicted in FIG. 5 (core shape variable).

Example 4: Characterization

FIG. 6A depicts a mechanism of preparing 3,4,5-tris (octadecaloxy)benzoic acid and new nonionic surfactant derivatives, such as HCBTS, HCBTO, and HCBTDE. The FTIR spectrum of the prepared compound ODEBA showed broad bands at 3277 centimeter inverse ($cm^{-1}$) for OH stretching, bands at (2855,2925) $cm^{-1}$ for $cp^3$ C—H stretching, bands at 3004 $cm^{-1}$ for $sp^2$ C—H stretching and bands at 1710 $cm^{-1}$ for C═O carboxylic carbonyl. In addition to the appearance of bands at 1614 $cm^{-1}$ for C═C stretching, band at 1430 $cm^{-1}$ for aromatic C═C (benzene ring), and broad bands at 1200 $cm^{-1}$ for C—O stretching as shown in FIG. 6B. The $^1H$ NMR spectra for the ODEBA showed major signals for (—CH$_3$) at δ 0.83; (—CH$_2$—) at δ 1.13-1.29; (—CH$_2$—CH$_2$—COO—) at δ 1.46; (—CH$_2$—CH═CH—) at δ 1.99; (—CH$_2$—CO—O—) at δ 2.14; (CH═CH—CH$_2$—CH═CH—) at δ 2.70; (—CH═CH—) at δ 5.26-5.47; (Ar ring) at δ 6.91-7.53 as shown in FIG. 7. Also, $^{13}C$ NMR spectra for compound ODEBA showed major carbon signals at δ 14.1 to (—CH$_3$); δ 22.6 to (—CH$_2$—CH$_3$); δ 24.9 to (CH$_2$—CH$_2$—COO—); δ 25.6 to (—CH═CH—CH$_2$—CH═CH—); δ 27.1 to (CH$_2$—CH═CH—); δ 29.0-29.6 to (—CH$_2$—); δ 31.8 to (CH$_3$—CH$_2$—CH$_2$—); δ 34.0 to (—CH$_2$—CO—O—); δ 109.1-145.8 to (C Ar ring); δ 128.0 to (—CH═CH—CH$_2$—CH═CH—); δ 129.9 to (—CH═CH—); δ 167.9 to (—COOH) and δ 174.8 to (—COO—Ar—) as shown in FIG. 8.

The FTIR spectrum of the synthesized compound HCBTDE in FIG. 9 showed broad bands at (3350) $cm^{-1}$ for OH stretching, and by comparing it with the ODEBA compound, the carboxylic carbonyl bands disappeared, and distinct bands appeared at 1737 $cm^{-1}$ for ester carbonyl, bands at (3012) $cm^{-1}$ for $sp^2$ C—H stretching. In addition to the appearance of a band at (1534) $cm^{-1}$ for aromatic C═C (benzene ring) and broad bands at (1179) $cm^{-1}$ for C—O stretching. The $^1H$ NMR spectra for the HCBTDE showed major signals for (—CH$_3$) at δ 0.85; (—CH$_2$—) at δ 1.15-1.29; (—CH$_2$—CH═CH—) at δ 2.17; (—CH$_2$—OH) at δ 3.41; (—COO—CH$_2$—CH$_2$—OH) at δ 3.51; (—CH$_2$—CH$_2$—OH) at δ 4.46; (—CH═CH—) at δ 5.31 and at δ 6.91-7.78 for (Ar ring) as shown in FIG. 10. FIG. 11 shows the $^{13}C$ NMR spectra for compound HCBTDE showed major carbon signals at δ 14.3 to (—CH$_3$); δ 25.6 to (—CH═CH—CH$_2$—CH═CH—); δ 27.0 to (—CH$_2$—CH═CH—); δ 31.7 to (CH$_3$—CH$_2$—CH$_2$—); δ 34.1 to (—CH$_2$—CO—O—); δ 60.7 to (—CH$_2$OH); δ 66.3 to (—COO—CH$_2$CH$_2$OH); δ 109-146.0 to (C Ar ring); δ 128.0 to (—CH═CH—CH$_2$—CH═CH—); δ 130.6 to (—CH═CH—); δ 167.9 to (—Ar—COO—CH$_2$) and δ 175.0 to (—CH2-COO—).

Figure 12B:
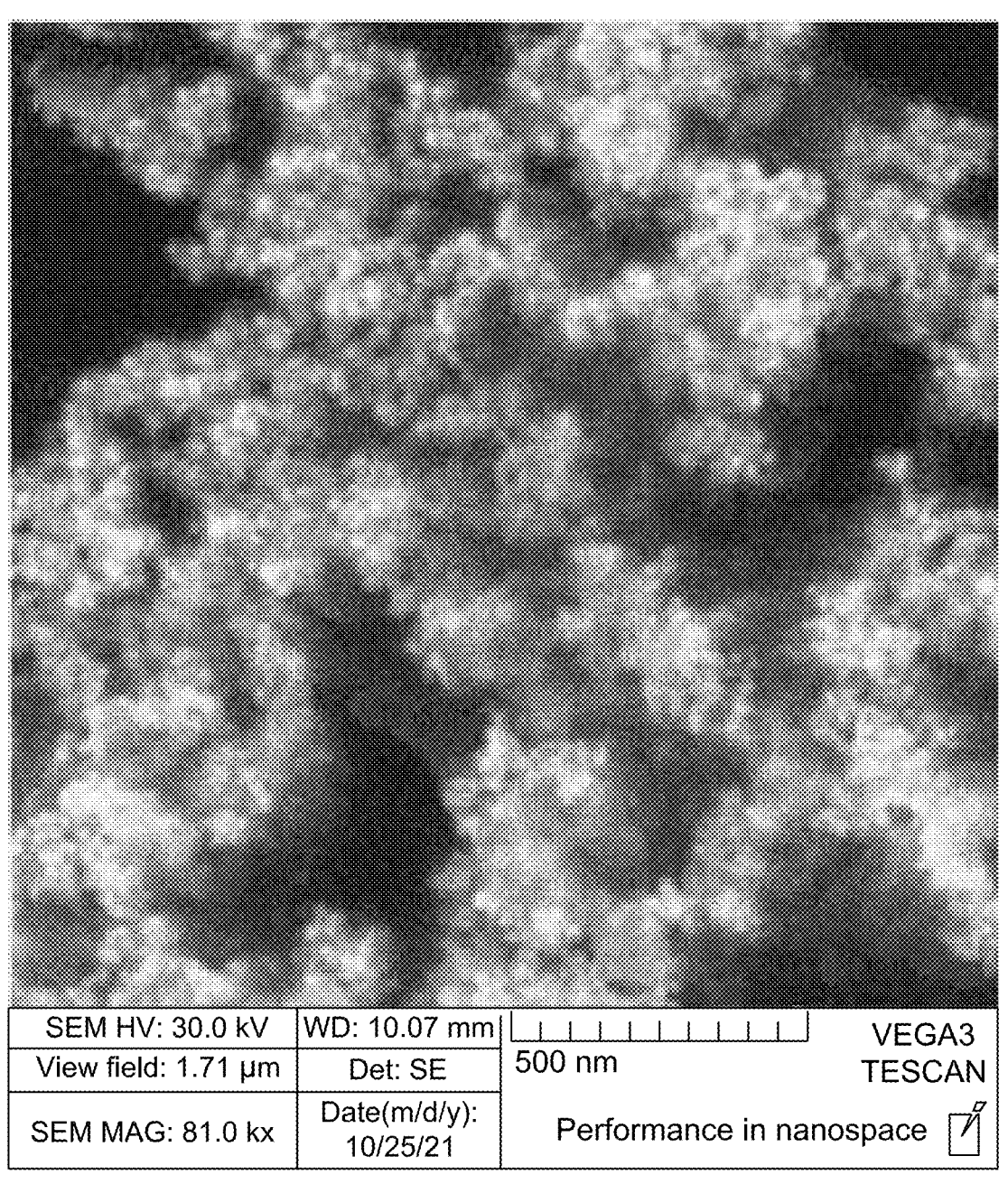
FIG. 12B depicts an SEM micrograph of 50 nanometers (nm) AuNPs at 0.5 μm scale, according to certain embodiments.
Figure 12C:
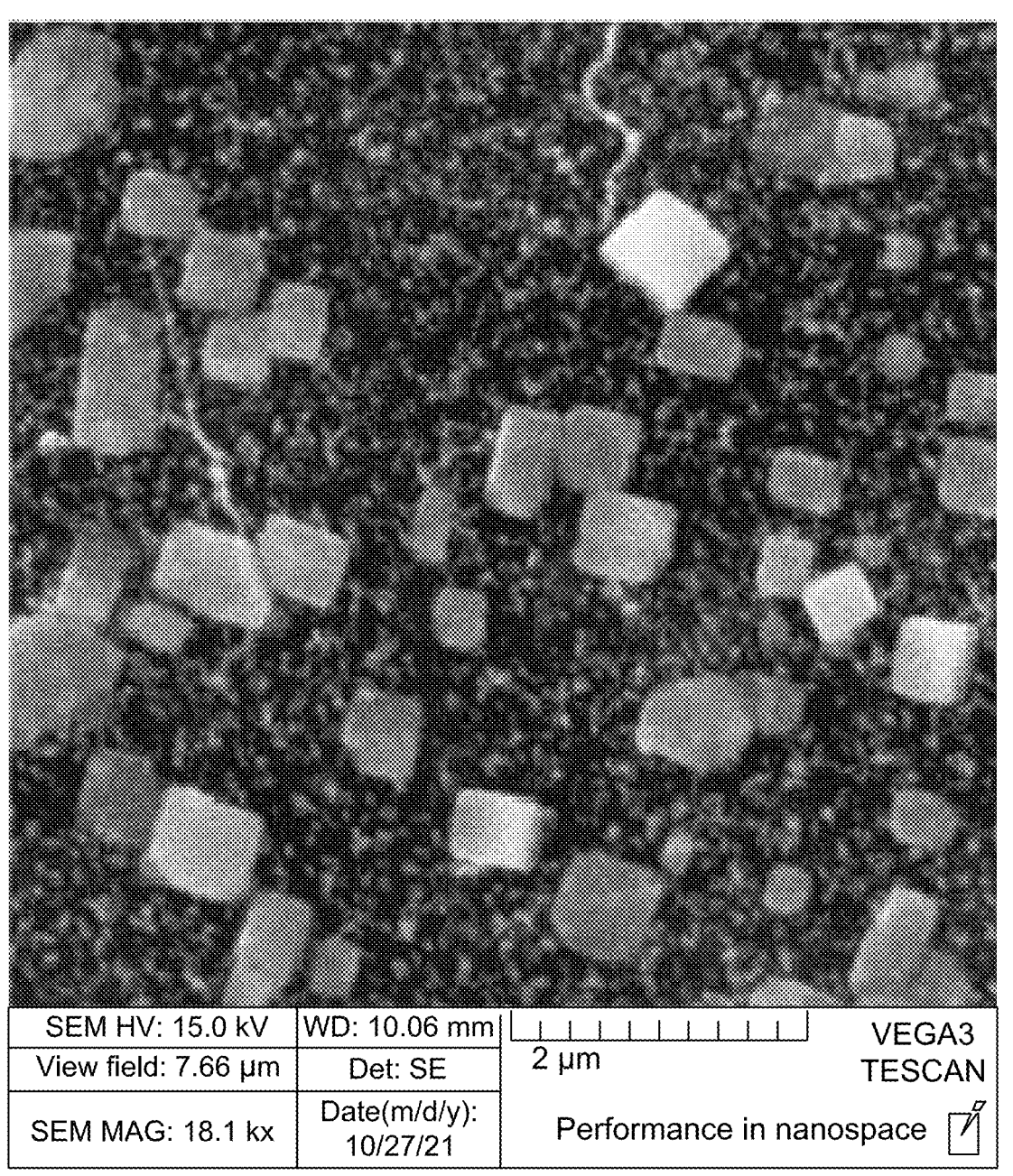
FIG. 12C depicts an SEM micrograph of AuNPs 35 nm sample at 2 μm scale, according to certain embodiments.
Figure 12D:
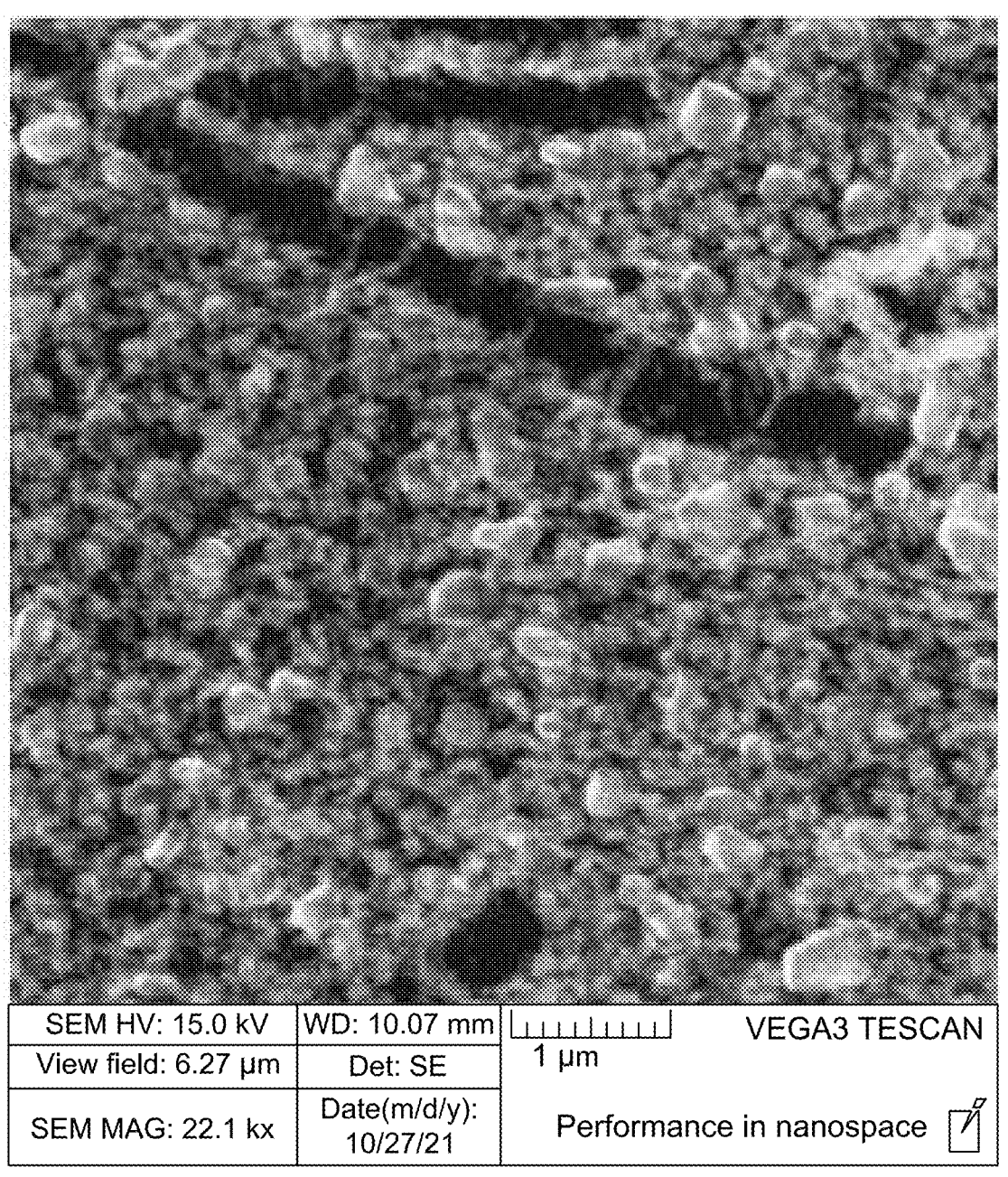
FIG. 12D depicts an SEM micrograph of AuNPs 35 nm sample at 1 μm scale, according to certain embodiments.
Figure 12E:
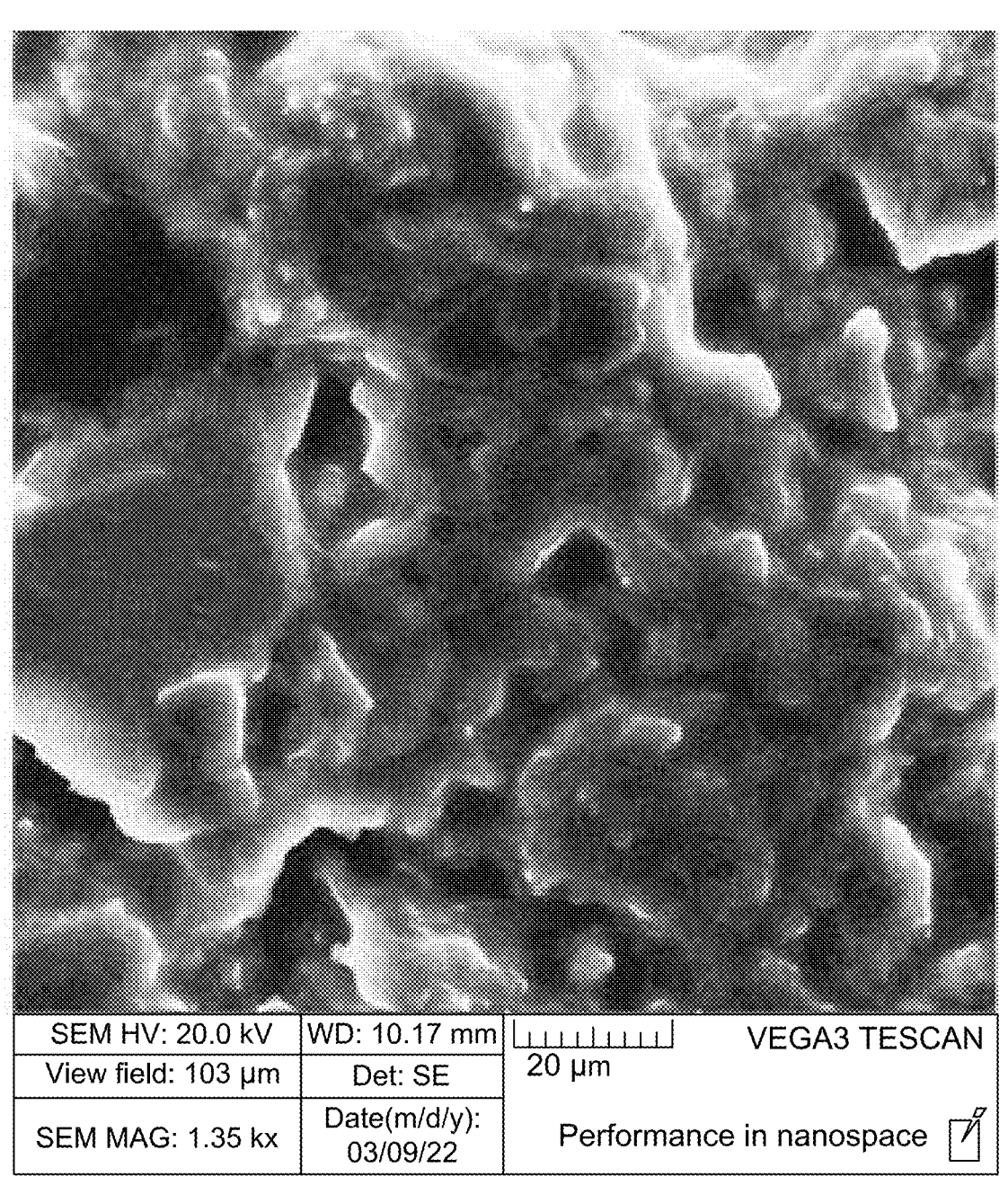
FIG. 12E-FIG. 12F depict an SEM micrographs AuNPs/HCBTDE at 20 μm scale, according to certain embodiments.
Figure 12F:
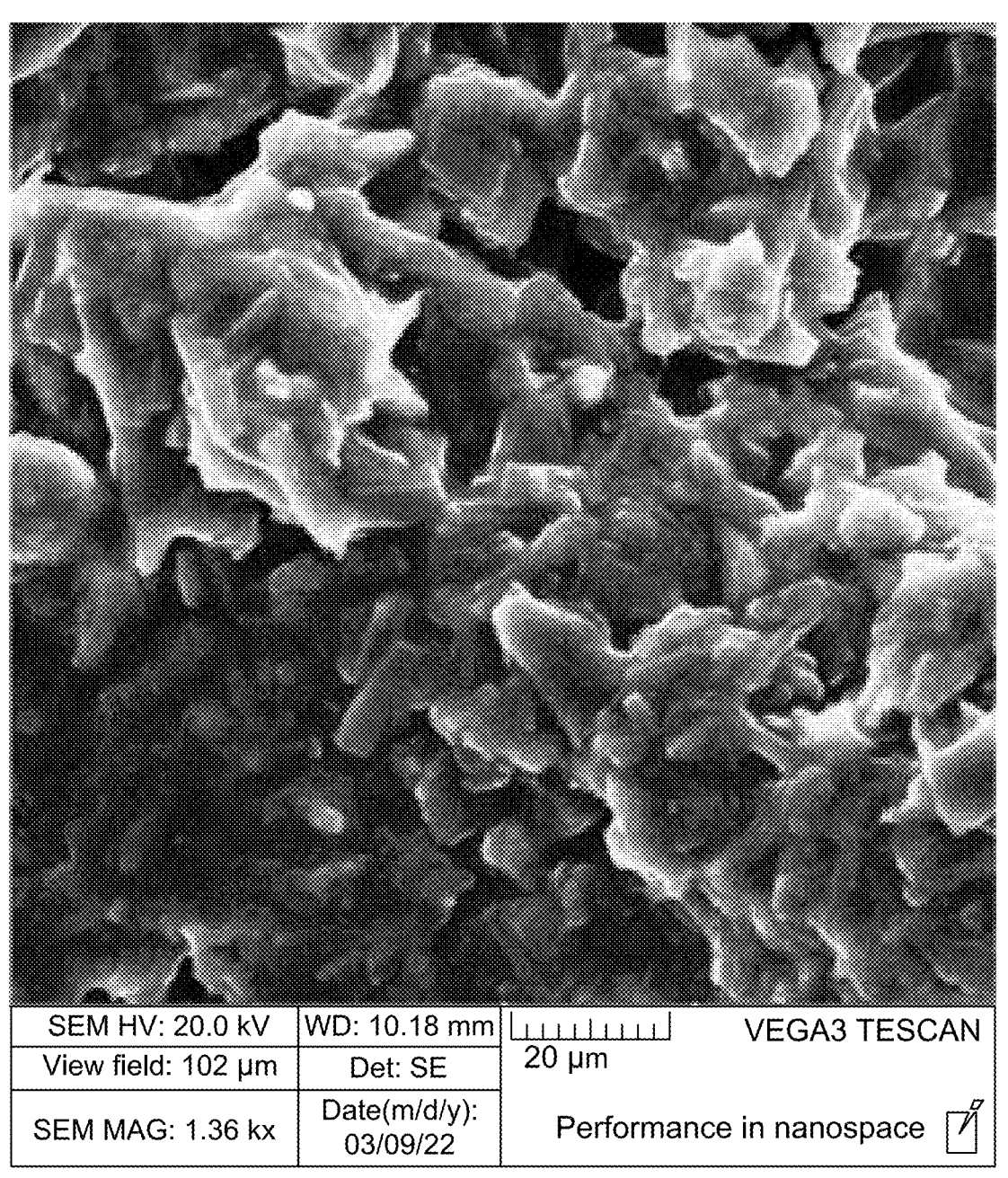

FIGS. 12A-12F show the magnified SEM micrographs of prepared 50 nm AuNPs (FIG. 12A and FIG. 12B), 35 nm AuNPs (FIG. 12C and FIG. 12D) and AuNPs/HCBTDE nanohybrid at different magnifications (0.5, 1, 2, 5 and 20 μm). The SEM image in FIG. 12A shows a clear and square crystal shape with different sizes. FIG. 12B shows the distribution of gold nanoparticles with small sizes of 50 nm AuNPs. In FIG. 12C and FIG. 12D, the 35 nm AuNPs show the smaller gold nanoparticles. FIG. 12E and FIG. 12F show that the AuNPs/HCBTDE nanohybrid contains different size sheets with a porous structure and different size sheets with high particle distribution of the gold nanohybrid. The presence of the gold signal was confirmed as depicted in FIGS. 13A-13B. The AuNPs contain different proportions of elements such as sodium, oxygen, chlorine, and gold. The EDS spectra clearly show the successful preparation of AuNPs.

FIG. 14 shows the UV spectrum of the synthesized gold nanoparticles with and without the addition of nonionic surfactant HCBTDE. A strong absorption peak appeared at 530 nm; however, adding surfactant HPDE to AuNPs dramatically changed their UV absorption spectra due to the accumulation of surfactant particles on the nanoparticles.

Example 5: Catalyst Test

The reduction of the hydrogenation of benzaldehyde was carried out under hydrogen flow on the catalyst at 160° C., and the obtained results are listed in Table 1. Before the reaction, the reaction temperature was kept constant during handling until the stationary mode was achieved. During this phase of the reaction, the equilibrium between the reactant's and the reaction's products' rates of adsorption and desorption allowed the catalysts to become stable.

The evolution of conversion as a function of temperature and material dose. These tests show that the catalyst has good efficiency. This may be due to the high adsorption of the molecules of the reagent due to the large specific surface area of the prepared gold nanohybrid and, possibly, due to the structure of the prepared material. The results in Table 1 show that the synthesized gold nanohybrid is more selective in benzyl alcohol at low temperatures, while more selectivity was observed in benzene at a high reaction temperature of 200° C., where this product is virtually non-existent at a low temperature of the reaction, but its selectivity tends to increase until it reaches a maximum by increasing the temperature.

At a high amount of gold nanohybrid, the formation of benzyl alcohol is much greater at the low amount of the modified gold and low temperature. At higher amounts of the modified gold and the reaction temperature of 200° C., the selectivity tends to decrease in favor of other benzene and toluene reaction products. This decline is more pronounced at the high temperature, showing that over time, the sites responsible for the formation of this product either deactivate or the intermediate species leading to the formation of alcohol re-arrange by transforming into toluene and benzene.

TABLE 1

The catalytic data obtained for the hydrogenation of
benzaldehyde over the catalyst .*

| Amount of the Material | Reaction Temperature (° C.) | Conversion** (%) | Selectivity*** (%) | | |
|---|---|---|---|---|---|
| | | | Benzyl alcohol | Toluene | Benzene |
| 25 mg | 100 | 23 | 88 | 4 | 8 |
| | 150 | 39 | 48 | 19 | 27 |
| | 200 | 61 | 5 | 15 | 82 |
| 50 mg | 100 | 26 | 85 | 6 | 9 |
| | 150 | 42 | 45 | 15 | 40 |
| | 200 | 63 | 6 | 6 | 88 |
| 75 mg | 100 | 29 | 82 | 5 | 13 |
| | 150 | 45 | 25 | 11 | 64 |
| | 200 | 64 | 5 | 4 | 91 |

*Reaction conditions: Catalyst:25, 50 and 75 mg, benzaldehyde: 4.8 torr, H₂: 250 torr.
**Determined by GC based on benzaldehyde at steady state.
***Determined by GC at steady state.

Numerous modifications and variations of the present disclosure are possible in light of the above teachings. It is, therefore, to be understood that within the scope of the appended claims, the invention may be practiced otherwise than as specifically described herein.

The invention claimed is:

1. A nanohybrid material, comprising:
a plurality of gold nanohybrid particles having formula (I);
wherein the gold nanohybrid particles have a gold nanoparticle (AuNPs) core and a shell of at least one fatty acid derivative at least partially disposed around the AuNPs core;
wherein the AuNPs core has a cuboidal shape and an average particle size of 20 to 60 nanometers (nm);
wherein formula (I) is Formula [I]

-continued wherein each $R_1$, and $R_2$ are independently selected from the group consisting of a hydrogen atom, and a fatty acid hydrocarbon chain having 16 to 22 carbon atoms;
wherein $R_3$ is selected from the group consisting of a hydrogen atom, an alkyl, an alkoxy, an optionally substituted alkoxy having 1 to 10 carbon atoms, and an optionally substituted alkoxyalky; and
n is any positive integer.

2. The nanohybrid material of claim 1, having a multi-layered porous structure.

3. The nanohybrid material of claim 2, wherein the multi-layered porous structure of the nanohybrid material has an average layer thickness of 60 to 500 nm.

4. The nanohybrid material of claim 1, having a pore size of 1 to 20 micrometers (μm).

5. The nanohybrid material of claim 1, wherein a weight ratio of the AuNPs core to the fatty acid derivative shell in the nanohybrid material ranges from about 1:10 to 1:50.

6. The nanohybrid material of claim 1, wherein the AuNPs core comprises Au nanoparticles having a plurality of carboxylate functional groups, wherein the at least one fatty acid derivative is connected to a carboxylate functional group of the plurality of carboxylate functional groups of the Au nanoparticles.

7. The nanohybrid material of claim 1, wherein the gold nanohybrid particles are uniformly distributed throughout the nanohybrid material and not forming aggregates.

8. The nanohybrid material of claim 1, wherein the gold nanohybrid particle is (9Z,9'Z,9"Z,12Z,12'Z,12"Z)-5-((2-hydroxyethoxy)carbonyl)benzene-1,2,3-triyl tris(octadeca-9,12-dienoate) (AuNPs/HCBTDE) having formula (II)

Formula [II]

and n is any positive integer.

9. A method of making the nanohybrid material of claim 8, comprising:

mixing and dissolving at least one fatty acid derivative having formula (III) in a first solvent to form a surfactant solution;

drop-wise adding the surfactant solution into a dispersion containing the AuNPs under continuous agitation to from a reaction mixture containing the nanohybrid material; and drying the reaction mixture to from the nanohybrid material;

wherein formula (III) is

Formula [III]

10. The method of claim 9, wherein a volume ratio of the surfactant solution to the dispersion is in a range of 1:2 to 1:10.

11. The method of claim 9, wherein the AuNPs present in the dispersion have an average particle size of 30 to 50 nm.

12. The method of claim 9, further comprising:

preparing the at least one fatty acid derivative of formula (III) by:

mixing a fatty acid and a trihydroxybenzoic acid in a second solvent in the presence of a sulfonic acid and refluxing to form a first product having formula (IV);

Formula [IV]

mixing the first product and ethylene glycol in the second solvent in the presence of a sulfonic acid and refluxing to form the at least one fatty acid derivative having formula (III).

13. The method of claim 12, wherein a molar ratio of the fatty acid to the trihydroxybenzoic acid is in a range of 2:1 to 1:2.

14. The method of claim 12, wherein a molar ratio of the first product to the ethylene glycol is in a range of 2:1 to 1:2.

15. The method of claim 12, wherein the fatty acid is octadeca-9,12-dienoic acid.

16. The method of claim 12, wherein the second solvent is xylene, and wherein the sulfonic acid is p-toluene sulfonic acid.

17. A method of benzaldehyde hydrogenation, comprising:

mixing and heating an aromatic aldehyde compound, and the nanohybrid material of claim 1 under a hydrogen flow thereby reducing the aromatic aldehyde compound with hydrogen molecules to form a reduction product;

wherein the reduction product is at least one selected from the group consisting of a substituted aromatic alcohol derivative, a substituted aromatic derivative, and an arene.

18. The method of claim 17, wherein up to 80 wt. % of the aromatic aldehyde compound is reduced to form the reduction product at a temperature of 100 to 200° C., each wt. % based on an initial weight of the aromatic aldehyde compound.

19. The method of claim 17, wherein a weight ratio of the nanohybrid material to the aromatic aldehyde compound is in a range of 1:200 to 1:10.

\* \* \* \* \*